(12) United States Patent
Fournial et al.

(10) Patent No.: US 9,126,060 B2
(45) Date of Patent: Sep. 8, 2015

(54) COSMETIC USE OF GERANYLGERANYL-2-PROPANOL

(75) Inventors: Arnaud Fournial, Paris (FR); Philippe Mondon, Cachan (FR); Olivier Peschard, Saint Prest (FR)

(73) Assignee: SEDERMA (FR)

( * ) Notice: Subject to any disclaimer, the term of this patent is extended or adjusted under 35 U.S.C. 154(b) by 0 days.

(21) Appl. No.: 13/639,933

(22) PCT Filed: Apr. 7, 2011

(86) PCT No.: PCT/IB2011/051498
§ 371 (c)(1),
(2), (4) Date: Oct. 8, 2012

(87) PCT Pub. No.: WO2011/125039
PCT Pub. Date: Oct. 13, 2011

(65) Prior Publication Data
US 2013/0058878 A1 Mar. 7, 2013

(30) Foreign Application Priority Data
Apr. 8, 2010 (FR) .................... 10 52676

(51) Int. Cl.
A61Q 17/04 (2006.01)
A61Q 19/08 (2006.01)
A61K 8/34 (2006.01)

(52) U.S. Cl.
CPC ............ *A61Q 17/04* (2013.01); *A61K 8/342* (2013.01); *A61Q 19/08* (2013.01)

(58) Field of Classification Search
USPC .................... 424/59; 514/739, 18.8
See application file for complete search history.

(56) References Cited

U.S. PATENT DOCUMENTS

| | | | |
|---|---|---|---|
| 5,385,938 A * | 1/1995 | Yu et al. | 514/557 |
| 6,372,717 B1 * | 4/2002 | Greff | 514/18.6 |
| 6,620,419 B1 | 9/2003 | Lintner | |
| 2004/0120918 A1 | 6/2004 | Lintner et al. | |
| 2004/0132667 A1 | 7/2004 | Lintner | |
| 2004/0156877 A1 * | 8/2004 | Tokuyama et al. | 424/401 |
| 2007/0178061 A1 * | 8/2007 | Venturi et al. | 424/74 |
| 2007/0185038 A1 * | 8/2007 | Bissett et al. | 514/25 |
| 2009/0041812 A1 * | 2/2009 | Bell | 424/401 |
| 2009/0214607 A1 | 8/2009 | Lintner et al. | |
| 2009/0269395 A1 * | 10/2009 | Lintner et al. | 424/450 |
| 2012/0076842 A1 | 3/2012 | Fournial et al. | |

FOREIGN PATENT DOCUMENTS

| | | |
|---|---|---|
| EP | 0046995 A1 | 3/1982 |
| EP | 1722864 A1 | 11/2006 |
| FR | 0953444 A | 12/1949 |
| FR | 2771002 A1 | 5/1999 |
| FR | 2854897 A1 | 11/2004 |
| FR | 2931651 A1 | 12/2009 |
| FR | 2945939 A1 | 12/2010 |
| JP | 57206691 A | 12/1982 |
| JP | 6192073 A | 7/1994 |
| JP | 10167957 A | 6/1998 |
| WO | 9407837 A1 | 4/1994 |
| WO | 98/07744 A1 | 2/1998 |
| WO | 99/25369 A1 | 5/1999 |
| WO | 9940897 A1 | 8/1999 |
| WO | 00/15188 A1 | 3/2000 |
| WO | 00/40611 A1 | 7/2000 |
| WO | 00/43417 A1 | 7/2000 |
| WO | 01/43701 A2 | 6/2001 |
| WO | 03/068141 A2 | 8/2003 |
| WO | 2007029187 A2 | 3/2007 |
| WO | 2009144680 A1 | 12/2009 |
| WO | 2010082175 A2 | 7/2010 |

OTHER PUBLICATIONS

JP 10-167957, Human Translation, 1998.*
International Search Report for Application No. PCT/IB2011/051498 dated Jan. 31, 2012.

* cited by examiner

*Primary Examiner* — Brian-Yong Kwon
*Assistant Examiner* — Jennifer A Berrios
(74) *Attorney, Agent, or Firm* — Lerner, David, Littenberg, Krumholz & Mentlik, LLP

(57) ABSTRACT

Geranylgeranyl-2-propanol compound (GGP) having the following formula I:

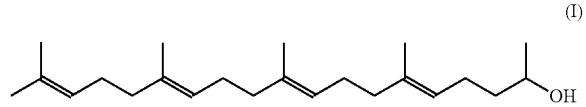

is proposed for use according to the present invention as a cosmetic active compound for the prevention and treatment of aging of skin and its appendages. The GGP has a protective action against oxidative stress and free radical, on telomeres and on mitochondria and its activity. In particular, GGP can be used for the treatment of wrinkles, fine lines and visible discontinuities of skin, for the treatment pigmentation disorders.

19 Claims, 1 Drawing Sheet

| T0 | T 1 month | T 2 months |
|---|---|---|
| FOITS | | FOITS |
| Prints | Prints | |
| Photographs +/- evaluation | Photographs +/- evaluation | Photographs +/- evaluation |
| Aeroflexmeter® | | Aeroflexmeter® |
| Echography | | Echography |

SEQUENCE LISTING

```
<160> NUMBER OF SEQ ID NOS: 11

<210> SEQ ID NO 1
<211> LENGTH: 6
<212> TYPE: PRT
<213> ORGANISM: artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: AMIDATION, Pal (C16). Seq description
      Pal-Val-Gly-Val-Ala-Pro-Gly.

<400> SEQUENCE: 1

Val Gly Val Ala Pro Gly
1               5

<210> SEQ ID NO 2
<211> LENGTH: 5
<212> TYPE: PRT
<213> ORGANISM: artificial sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: AMIDATION, Pal (C16). Seq description
      Pal-Lys-Thr-Thr-Lys-Ser

<400> SEQUENCE: 2

Lys Thr Thr Lys Ser
1               5

<210> SEQ ID NO 3
<211> LENGTH: 4
<212> TYPE: PRT
<213> ORGANISM: artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: AMIDATION, Pal (C16). Seq description
      Pal-Gly-Gln-Pro-Arg

<400> SEQUENCE: 3

Gly Gln Pro Arg
1

<210> SEQ ID NO 4
<211> LENGTH: 5
<212> TYPE: PRT
<213> ORGANISM: artificial sequence
<220> FEATURE:
<223> OTHER INFORMATION: Synthetic peptide

<400> SEQUENCE: 4

Lys Thr Thr Lys Ser
1               5

<210> SEQ ID NO 5
<211> LENGTH: 4
<212> TYPE: PRT
<213> ORGANISM: artificial sequence
<220> FEATURE:
<223> OTHER INFORMATION: synthetic peptide

<400> SEQUENCE: 5

Arg Ser Arg Lys
1

<210> SEQ ID NO 6
<211> LENGTH: 4
<212> TYPE: PRT
<213> ORGANISM: artificial sequence
<220> FEATURE:
<223> OTHER INFORMATION: synthetic peptide

<400> SEQUENCE: 6

Gly Gln Pro Arg
1

<210> SEQ ID NO 7
<211> LENGTH: 4
<212> TYPE: PRT
<213> ORGANISM: artificial sequence
<220> FEATURE:
<223> OTHER INFORMATION: synthetic peptide

<400> SEQUENCE: 7
```

```
Lys Thr Phe Lys
1

<210> SEQ ID NO 8
<211> LENGTH: 6
<212> TYPE: PRT
<213> ORGANISM: artificial sequence
<220> FEATURE:
<223> OTHER INFORMATION: synthetic peptide

<400> SEQUENCE: 8

Gly Lys Thr Thr Lys Ser
1               5

<210> SEQ ID NO 9
<211> LENGTH: 6
<212> TYPE: PRT
<213> ORGANISM: artificial sequence
<220> FEATURE:
<223> OTHER INFORMATION: Synthetic peptide

<400> SEQUENCE: 9

Val Gly Val Ala Pro Gly
1               5

<210> SEQ ID NO 10
<211> LENGTH: 5
<212> TYPE: PRT
<213> ORGANISM: artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: AMIDATION, Pal (C16). Seq description
      Pal-Tyr-Gly-Gly-Phe-Met

<400> SEQUENCE: 10

Tyr Gly Gly Phe Met
1               5

<210> SEQ ID NO 11
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: AMIDATION, Pal (C16). Seq description
      Pal-Tyr-Gly-Gly-Phe-Met

<400> SEQUENCE: 11

Tyr Gly Gly Phe Leu
1               5
```

COSMETIC USE OF GERANYLGERANYL-2-PROPANOL

CROSS-REFERENCE TO RELATED APPLICATIONS

The present application is a national phase entry under 35 U.S.C. §371 of International Application No. PCT/IB2011/051498 filed Apr. 7, 2011, published in English, which claims priority from French Application No. 1052676 filed Apr. 8, 2010, all of which are incorporated herein by reference.

TECHNICAL FIELD

The subject matter of the present invention is a new application of the geranylgeranyl-2-propanol. The present invention concerns more particularly personal care and cosmetic industries for skin and appendages (like hair, eyelashes, eyebrows, nails, hairs) of human or animal mammals.

BACKGROUND ART

Geranylgeranyl-2-propanol (6,10,14,18-tetramethylnonadeca-5,9,13,17-tetraen-2-ol) corresponds to the terpenic alcohol having the developed following formula I:

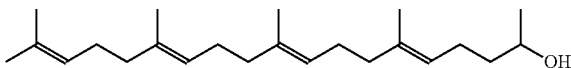 [SMILES: CC(C)=CCC/C(C)=C/CC/C(C)=C/CC/C(C)=C/CCC(C)O]

Geranylgeranyl-2-propanol is a derivative of isoprene; isoprenes are complex lipids comprising in particular a geranylgeranyl polyterpenic chain. Coupled to numerous cellular proteins, isoprenoids, like the geranylgeranylphosphate or the farnesylphosphate, regulate the activity of these proteins and their location in the different cellular compartments as well. The coupling is done by a transferase that uses the energy released during the breaking of the phosphate bond of the isoprene-PO4 squeleton.

In general, these lipids promote by their presence the protein interactions in accompanying their mobility within the cell and mitochondrial lipid membranes. The basic structure of geranylgeranyl, by its role, appears somewhat like a metabolism facilitator. Geranylgeranyl-2-propanol (hereinafter referred to the GGP in the description) has already been cited in the document JP10167957 as likely to treat disorders of the stratum corneum, that is to say, the outermost layer of skin, via an inhibitory activity of the formation of desmosomes in the epidermis. The general aim of the present invention is to meet the ever increasing demand for new compounds more efficient to fill the desire of many people of retaining or regaining a youthful appearance.

SUMMARY OF THE INVENTION

Therefore, the subject matter of the present invention is the geranylgeranyl-2-propanol compound (GGP) having the formula I for use as a cosmetic active compound for the cosmetic and non therapeutical treatment of aging of the skin and its appendages.

As detailed below, the geranylgeranyl-2-propanol (GGP) compound is particularly active against oxidative stress, has a protective action of telomeres and mitochondria and promotes the synthesis of molecules of the extracellular matrix (ECM), collagen I, hyaluronic acid and decorin.

Skin and appendages aging is due to endogenous factors (natural aging time) and to exogenous factors such as UV radiation from the sun, pollution, climatic conditions or stress. It will result in a deterioration of original properties of the skin. The most visible signs of this degradation include unsightly wrinkles and fine lines, sagging skin which loses its firmness and elasticity, thinning skin, loss of brightness (occurrence of spots, loss of uniformity), the increase in pore size, rednesses, dull hair, hair loss, etc.

At the biological level, these macroscopic observations lead into changes associated with declining vitality of tissues and cells, slowing of the replication and therefore of the cell renewal, decreased protein synthesis, increased proteolysis, an accumulation of errors in the synthesis, depletion and disorganization of the fibers of the extracellular matrix. At a molecular level, it is essentially the accumulation of radical oxygen species (ROS) which is the origin of biochemical disorders responsible for aging. Whether induced by exogenous or endogenous factors, free radicals will cause skin inflammation and skin aging. In "normal" conditions, on a skin young, healthy and relatively protected from external aggression, there is a balance between the production of reactive oxygen species (ROS) in the organism and the antioxidant defenses responsible for neutralizing them. These defense systems are made either by enzymes (SOD, catalase, glutathione peroxidase) or by conventional antioxidants (vitamin C, vitamin E, glutathione, carotene etc.). When a punctual imbalance occurs, there is a massive production of reactive oxygen species (ROS), too important for the defense capabilities of the organism, causing an oxidative stress. It will always result in damage to DNA, proteins, unsaturated fats and sugars cell, which will undergo oxidation, causing alterations in their structure and function. Over time and imbalances, the defense systems are deteriorating and shrinking, which has the effect of increasing the general level of oxidative stress, the main factor of aging.

Within the human cell, the negative effects of aging are felt mainly in the mitochondria which lose their ability to produce ATP, the main energy source in the cell, and telomeres, which continuous erosion leads to the cessation of cell divisions.

The compound of the invention has the particularity, as evidenced by the Applicant, to protect the mitochondria against the adverse effects of aging.

Human cells synthesize the components necessary for the proper functioning and development of the organism, eliminate waste, defend themselves against aggressions, and divide. The realization of these functions requires energy. The primary role of mitochondria is to produce ATP (adenosine tri phosphate) from AMP, ADP and phosphate. In all living organisms, the ATP molecule provides, during its hydrolysis, the energy required for chemical reactions of cells. Its production will be done in two steps. As a first step, acetyl CoA, derived from the breakdown of glucose and fatty acid enters the Krebs cycle, where it is dehydrogenated by providing reduced cofactors FADH2, NADH, and $CO_2$.

In a second step, at the level of the inner membrane of mitochondria, an electron transport chain involving several enzyme complexes, called: NADH-quinone oxidoreductase (complex I), succinate-quinone oxidoreductase (complex II), quinol-cytochrome c oxidoreductase (complex III or complex bc1) and cytochrome c oxidase (complex IV) will allow the capture of electrons from FADH2 and NADH, with the simultaneous transfer of protons ($H^+$) across the membrane to create a proton gradient, and $H_2O$ formation from molecular $O_2$.

The electrochemical gradient thus generated is used for phosphorylation of ADP to ATP by ATP synthase. The coupling of oxidation metabolites of $CO_2$ and $H_2O$ and ATP production is called oxidative phosphorylation. The importance of this phenomenon can be given by the fact that the human body produces its own weight of ATP every day. Mitochondria, through cellular respiration, thus transform molecular oxygen into water. This transformation, however, is never perfect and is accompanied in 0.2 to 2% of the reactions by "failures" thereby creating the superoxide anion ($O_2\bullet^-$) instead of molecular oxygen O2. Even in normal conditions, 80% of the production of $O_2\bullet^-$ is the result of these "failed" reactions. The $O_2\bullet^-$ is the precursor of hydrogen peroxide ($H_2O_2$) which can in turn give rise to other more reactive radical species, including the highly oxidizing hydroxyl radical (OH•). These highly reactive species react with the living macromolecules (proteins, lipids, sugars, DNA) to change them, inducing mutations in DNA, disruption of lipid membranes, alteration of functional proteins, sugars, DNA etc.

With age, there is increased production of this radical production in the mitochondria. The radicals will gradually damage the internal membranes, the location of oxidative phosphorylation, the respiratory complexes and the mitochondrial DNA. Thus, natural or induced aging reduces the performance of the mitochondria respiratory by action at these different levels.

The result is in an increasing loss of efficiency in the mitochondrial ATP production which has the effect of reducing the energy supplied to the cell to manufacture the biological macromolecules for defending, eliminating waste and radical species and multiplying. The downward spiral of aging is then begun.

In addition to this damaging loss of energy, the entire cell is also affected by the dysfunction of mitochondrial respiration via the hydrogen peroxide and reactive oxygen species (ROS) produced more significantly by the aging mitochondria and that will diffuse into the cytoplasm and the nucleus, through the mitochondrial membrane. Cellular DNA is subject such as the mitochondrial DNA to the oxidation of its bases and will undergo mutations. It is the same for proteins, sugars and lipids, the other major cellular constituents, whose oxidation will cause metabolic dysfunctions, structural changes, affecting the cell and cause aging. It appears from recent researches that it is the alteration of the functioning of mitochondria, which over time will generate more oxygen free radicals, and consequently a less efficient breathing and a general oxidation of cellular components (proteins, DNA, lipids) responsible for aging. Hence there is a clear need for an anti-aging cosmetic product to act against these oxygen free radicals within the mitochondria. This is precisely the mode of action that was demonstrated for the compound of the invention on human dermal fibroblasts.

The GGP compound of the invention also has the feature, highlighted by the Applicant, to protect the telomers against the negative effects of aging.

Chromosomes, made up of DNA, comprise at their ends highly repetitive noncoding regions called telomeres. Telomeres are not involved in protein synthesis, but have a protective role of chromosome ends and play a major role in the replication capacity of the cell. In humans, telomeres are sequences of 3-20 kb with repetitions of the motif TTAGGG. As the divisions go along, the telomere is not fully copied and therefore shortens, without the possibility of being repaired at least in somatic cells.

This erosion of telomeres over time affects the stability of chromatin and finally impairs his division capacity. In cell culture, when telomeres have shortened sufficiently, cell division is no longer possible; the cell enters into senescence and finally dies. This is true also in vivo, in the organism, where telomere shortening with age was observed in all examined somatic cells.

Some environmental factors can accelerate the erosion of telomeres. Using data from both in vitro and in vivo, it is apparent that this erosion is even stronger when the cells (for the in vitro) or the person (for the in vivo) are subjected to an important oxidative stress. Among the factors causing oxidative stress, all inflammatory conditions, such as smoking, can be mentioned. Psychological stress is also strongly suspected to increase oxidative stress.

Thus, the average length of telomeres in a living organism is a good marker of biological age of the cells. It is primarily a reflection of a genetically programmed evolution specific for each person. This evolution will be modulated according to the particular circumstances of life (fatigue, psychological stress, pollution encountered). The biological age will be in fine the result of endogenous and exogenous factors, natural cellular senescence, based on a gradual decline in telomere length in each division, will be enhanced by the alteration of these telomeres induced by the oxidative stress.

That's why the cosmetic industry is looking for compounds able to limit the shortening of telomeres, in order to delay cellular aging.

The GGP compound of the invention acts in this way on human dermal fibroblasts. The inventors have also shown that the GGP was acting on the molecules of the extracellular matrix, particularly by stimulating the synthesis of collagen I, hyaluronic acid and decorin.

A cause of dermal aging is the decrease of collagen synthesis (1% per year from age 20). This partly explains the gradual decrease of the thickness, firmness and elasticity of the dermis and thus of the skin, over time. For this reason, it is now recognized the value of stimulating the synthesis of collagen in fibroblasts, to slow skin aging. The compound of the invention acts in this direction on human dermal fibroblasts.

On its side, hyaluronic acid is one of the main constituents of the dermis and epidermis. It has a very large capacity to capture and retain water. With age the skin loses hyaluronic acid (−50% between age 20 and 50), resulting in dry skin and occurrence of wrinkles. Through the stimulation of hyaluronic acid synthesis, the effects of aging by increasing the hydration and elasticity of the skin, by restoring volume to emaciated skin and by filling wrinkles and fine lines, are fighted. GGP owns this property of stimulating the synthesis of hyaluronic acid on human dermal fibroblasts.

Decorin in turn is a leucine rich glycoprotein that regulates the assembly of certain tissues. Mammals deficient in decorin exhibit fragile skin with immature collagen fibers. It has been shown that decorin is associated with tropoelastin and microfibrils. Its production is interesting at the level of the extracellular matrix as a "companion" of collagen fibers that coexist with the elastic fibers to give to the dermis its strength and elastic and mechanical properties.

It was observed that there is no overall loss of pigmentation with age. The skin of a person exposed to the sun on a regular basis is usually more pigmented than that of a young subject, and despite a lower density of melanocytes. This paradox is explained by the highest activity among older melanocytes, after several years of cumulative sun exposure. However, on older skin, it is common to observe the appearance of unsightly brown spots in areas that have been exposed to the sun. This phenomenon is linked to an increased activity of tyrosinase, leading to overproduction of melanin. The Applicant has found that the compound of the invention has a property of inhibiting tyrosinase activity and melanin synthesis to help limit the occurrence and intensity of these spots.

The Applicant therefore proposes the geranylgeranyl-2-propanol (GGP), a lipid complex, for use as a cosmetic active ingredient in different key levels of skin aging:

By protecting the energy unit of the cell and its ability to produce ATP (acting on the mitochondria);

By limiting the shortening of telomeres;

By stimulating the synthesis of collagen, hyaluronic acid and decorin (action on the matrix synthesis);

By acting on the junction epidermis/dermis via the synthesis of Nidogen 1;

By acting on disorders of pigmentation;

By protecting keratinocytes against UVB radiations.

The inventors have thus demonstrated that the GGP can be used in a cosmetic composition and that the GGP is particularly suited:

To delay the aging of the skin with a protective effect on telomeres and mitochondria and in particular with a protective action against oxidative stress and free radicals. Skin is protected.

To treat skin aging through a remedial action of wrinkles, fine lines and visible discontinuities of the skin and/or treating the weakening of the mechanical properties of the skin (loss of firmness and elasticity of the skin) through action on the synthesis of molecules of the skin extracellular matrix and on the contraction capacity of fibroblasts. The skin is denser, firmer, softer and more elastic. Wrinkles and fine lines are less visible.

To treat pigmentation disorders (the occurrence of pigmentation spot) thanks to an inhibitory action on melanogenesis. Complexion is more homogeneous and brighter.

To protect keratinocytes against UVB.

On appendages, the effects are also visible: in particular the hair is less dull and nails less brittle.

The inventors have thus demonstrated that the GGP is a remarkable compound for its global "anti-aging" action both from a prevention perspective and a treating perspective on the skin and its appendages. The GGP can also be used for its anti-inflammatory action (in particular for treating rednesses), antioxidant or antiradical activity, depigmentation activity, protective against UVB, regardless of the stage of skin aging.

The GGP can be obtained for example by chemical synthesis, especially from geranyl linalool or other starting polyterpenic compounds.

Results of in vitro and in vivo tests obtained with the GGP are further detailed in the description. The present invention proposes a composition containing the GGP as active compound in a physiologically acceptable medium for the prevention and treatment of skin and appendages aging.

According to other advantageous features, the cosmetic composition of the invention may incorporate one or more additional active compounds, to provide advantageously a cosmetic product with a wider range of properties or to enhance the properties of the compounds of the present invention. Additional active compounds may for example be selected from the lightening, anti-redness, sunscreens, moisturizing, humectants, exfoliating, anti-aging, anti-wrinkle and fine lines, slimming, stimulating the collagen and/or elastin synthesis, volumizing, elastic properties improving, anti-acne, anti-inflammatory, antioxidants, anti-free radical, depigmenting agents, depilatories, anti-regrowth or promoting the growth agents, peptides, vitamins etc. These active compounds may be obtained from plant materials such as plant extracts or products from plant cells culture or fermentation.

More specifically, the GGP compound of the invention can be combined with at least one of compounds selected from compounds of vitamin B3, niacinamide compounds like or tocopherol, retinol, hexamidine, .alpha.-lipoic acid, resveratrol or DHEA or N-acetyl-Tyr-Arg-O-hexadecyl, Pal-KT, Pal-VGVAPG (SEQ ID NO: 1), Pal-KTTKS (SEQ ID NO: 2), Pal-GHK, Pal-KMO$_2$K and Pal-GQPR (SEQ ID NO: 3) peptides, which are active ingredients widely used in cosmetic or dermo-cosmetical topical compositions.

The invention proposes furthermore a method of treating the aging skin comprising topically applying the composition according to the invention to the skin of a subject in need thereof.

BRIEF DESCRIPTION OF THE DRAWINGS

FIG. 1 depicts a flow chart of a study evaluating the anti-aging efficacy of a composition comprising GGP at 0.04%.

DETAILED DESCRIPTION

The term "physiological medium" means according to the present invention, without limitation, an aqueous or alcoholic solution, a water-in-oil emulsion, an oil-in-water emulsion, a microemulsion, an aqueous gel, an anhydrous gel, a serum, a dispersion of vesicles.

"Physiologically acceptable" means that the disclosed compositions or compounds are suitable for use in contact with mucous membranes, nails, scalp, hairs, hair and skin of mammals and more particularly human without risk of toxicity of incompatibility, instability, allergic response, and others.

When present in a composition, the GGP compound of the invention is present in amounts ranging from 0.000001% to 15% w/w compared to the total weight of the composition, more preferably between 0.0001% and 10% w/w, depending of the destination of the composition and the desired effect more or less pronounced.

All percentages and ratios used herein are by weight of total composition and all measurements are made at 25° C. unless it is specified otherwise.

Typically, in a composition of the invention consisting simply of the GGP compound of the invention and of an excipient (the physiologically medium) used as solubilizer, for example, forming an "active ingredient" for the future preparation of a cosmetic formulation, the amount of the compound will be comprised between 0.005% and 5% w/w.

The choice of the excipient of the composition is made according to the constraints related to the compounds of the invention (stability, solubility, etc.) and if according to the dosage form then considered for the composition.

The GGP compound can be solubilized with cosmetically, pharmaceutically or physiologically acceptable conventional solubilizers, preferably a hydrophobic matrix given its terpenic structure.

Additional Ingredients

The CTFA International cosmetic ingredient dictionary & handbook (13th Ed. 2010) (published by the Cosmetic, Toiletry, and Fragrance Association, Inc., Washington, D.C.) describes a non limited wide variety of cosmetic and pharmaceutical ingredients usually used in the skin care industry that can be used as additional ingredients/compounds in the compositions of the present invention. Examples of these ingredient classes include, but are not limited to: healing agents, skin anti-aging agents, anti-wrinkle agents, anti-atrophy agents, skin moisturizing agents, skin smoothing agents, antibacterial agents, pesticides anti parasitic agents, antifungal agents, fungicidal agents, fungi static agents, bactericidal agents, bacteriostatic agents, antimicrobial agents, anti-inflammatory agents, anti-pruriginous agents, external anesthetic agents, antiviral agents, keratolytic agents, free radicals scavengers, antiseborrheic agents, antidandruff agents, the agents modulating the differentiation, proliferation or pigmentation of the skin and agents accelerating penetration, desquamating agents, melanin synthesis stimulating or inhibiting agents, whitening or depigmenting agents, propigmenting agents, self-tanning agents, NO-synthase inhibiting agents, antioxidants, free radical scavengers and/or agents against atmospheric pollution, reactive carbonyl species scavengers, antiglycation agents, tightening agents, agents stimulating the synthesis of dermal or epidermal macromolecules and/or capable of inhibiting or preventing their degradation, such as for example collagen synthesis-stimulating agents, elastin synthesis-stimulating agents, decorin synthesis-stimulating agents, laminin synthesis-stimulating agents, defense synthesis-stimulating agents, chaperone synthesis-stimulating agents, aquaporin synthesis stimulation agents, hyaluronic acid synthesis-stimulating agents, fibronectin synthesis stimulating agents, sirtuin synthesis-stimulating agents, agents stimulating the synthesis of lipids and components of the stratum corneum (ceramides, fatty acids, etc.), agents that inhibit collagen degradation, other agents that inhibit elastin degradation, agents that inhibit serine proteases such cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, antihyperkeratosis agents, comedolytic agents, antipsoriasis agents, DNA repair agents, DNA protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating reepithelialization, coadjuvant reepithelialization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, muscle relaxants; antipollution and/or anti-free radical agents; lipolytic agents, venotonic agents, slimming agents, anticellulite agents, agents acting on the microcirculation; agents acting on the energy metabolism of the cells; cleaning agents, hair conditioning agents, hair styling agents, hair growth promoters, sunscreen and/or sunblock compounds, make-up agents, detergents, pharmaceutical drugs, emulsifiers, emollients, antiseptic agents, deodorant actives, dermatologically acceptable carriers, surfactants, abrasives, absorbents, aesthetic components such as fragrances, colorings/colorants, essential oils, skin sensates, cosmetic astringents, anti-acne agents, anti-caking agents, anti foaming agents, antioxidants, binders, biological additives, enzymes, enzymatic inhibitors, enzyme-inducing agents, coenzymes, chelating agents, plant extracts, plant derivatives, plant tissue extracts, plant seed extracts, plant oils, botanicals, botanical extracts, essential oils, marine extracts, agents obtained from a biofermentation process, mineral salts, cell extracts and sunscreens (organic or mineral photoprotective agents active against ultraviolet A and/or B rays), ceramides, peptides, buffering agents, bulking agents, chelating agents, chemical additives, colorants, cosmetic biocides, denaturants, drug astringents, external analgesics, film formers or materials, e.g., polymers, for aiding the film-forming properties and substantivity of the composition, quaternary derivatives, agents increasing the substantivity, opacifying agents, pH adjusters, propellants, reducing agents, sequestrants, skin bleaching and lightening agents, skin tanning agents, skin-conditioning agents (e.g., humectants, including miscellaneous and occlusive), skin soothing and/or healing agents and derivatives, skin treating agents, thickeners, and vitamins and derivatives thereof, peeling agents, moisturizing agents, curative agents, lignans, preservatives, UV absorbers, a cytotoxic, an antineoplastic agent, a fat-soluble active, suspending agents, viscosity modifiers, dyes, nonvolatile solvents, diluents, pearlescent aids, foam boosters, a vaccine, and their mixture.

The additional active ingredient/compound can be selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, peptides and their derivatives, di-, tri-, tetra-, penta-, and hexapeptides and their derivatives, in particular acyl derivatives, KTTKS (SEQ ID NO: 4), PalKTTKS (SEQ ID NO: 2), carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins their salts and derivatives, provitamins and their salts and derivatives, ethyl panthenol, vitamin B, vitamin B derivatives, vitamin B1, vitamin B2, vitamin B6, vitamin B12, vitamin K, vitamin K derivatives, pantothenic acid and its derivatives, pantothenyl ethyl ether, panthenol and its derivatives, dexpanthenol, biotin, amino acids and their salts and derivatives, water soluble amino acids, asparagine, alanine, indole, glutamic acid, water insoluble vitamins, vitamin A, vitamin E, vitamin F, vitamin D, mono-, di-, and tri-terpenoids, beta-ionol, cedrol, and their derivatives, water insoluble amino acids, tyrosine, tryptamine, butylated hydroxytoluene, butylated hydroxyanisole, allantoin, tocopherol nicotinate, tocopherol, tocopherol esters, pal-GHK, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, particulate materials, pigment materials, natural colors, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and its salts, dihydroxyacetone, erythrulose, glyceraldehyde, tartaraldehyde, clove oil, menthol, camphor, eucalyptus oil, eugenol, menthyl lactate, witch hazel distillate, eicosene and vinyl pyrrolidone copolymers, iodopropyl butylcarbamate, a polysaccharide, an essential fatty acid, salicylate, glycyrrhetinic acid, carotenoides, ceramides and pseudo-ceramides, a lipid complex, oils in general of natural origin such shea butter, apricot oil, onagre oil, prunus oil, palm oil, monoi oil, HEPES, procysteine, O-octanoyl-6-D-maltose, the disodium salt of methylglycinediacetic acid, steroids such as diosgenin and derivatives of DHEA, DHEA or dehydroepiandrosterone and/or a precursor or chemical or biological derivative, N-ethyloxycarbonyl-4-para-aminophenol, bilberry extracts; phytohormones; extracts of the yeast *Saccharomyces cerevisiae*, extracts of algae, extracts of soyabean, lupin, maize and/or pea, alverine and its salts, in particular alverine citrate, extract of butcher's broom and of horse chestnut, and mixtures thereof, a metallopreoteinase inhibitor.

Further skin care and hair care active ingredients that are particularly useful can be found in SEDERMA commercial literature and on the website www.sederma.fr.

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

The following known actives can be mentioned, as examples: betain, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Essenskin™ (Sederma), Moist 24™ (Sederma), Argireline™ (trade name of the acetyl hexapeptide-3 of Lipotec), spilanthol or an extract of *Acmella oleracea* known under the name Gatuline Expression™ (EP 1722864), an extract of *Boswellia serrata* known under the name Boswellin™ Deepaline PVB™ (Seppic), Syn-AKE™ (Pentapharm), Ameliox™, Bioxilift™ (Silab) or mixtures thereof.

Among other plant extracts which can be combined with the GGP compound of the invention, there may more particularly be mentioned extracts of Ivy, in particular English Ivy (*Hedera Helix*), of Chinese thorowax (*Bupleurum chinensis*), of *Bupleurum Falcatum*, of arnica (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hypericum Perforatum*), of butcher's-broom (*Ruscus aculeatus* L), of European meadowsweet (*Filipendula ulmaria* L), of bigflowered Jarva tea (*Orthosiphon Staminicus Benth*), of algae (*Fucus Vesiculosus*), of birch (*Betula alba*), of green tea, of cola nuts (*Cola Nipida*), of horse-chestnut, of bamboo, of spadeleaf (*Centella asiatica*), of heather, of fucus, of willow, of mouse-ear, of escine, of cangzhu, of chrysanthellum indicum, of the plants of the *Armeniacea* genus, *Atractylodis Platicodon, Sinnomenum, Pharbitidis, Flemingia*, of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, of *Guioa*, of *Davallia*, of *Terminalia*, of *Barringtonia*, of *Trema*, of *antirobia, cecropia, argania, dioscoreae* such as *Dioscorea opposita* or Mexican, extracts of *Ammi visnaga*, of *Centella asiatica* and *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, *Piper* methysticum extract (Kava Kava from SEDERMA (FR 2 771 002 and WO 99/25369), *Bacopa monieri* extract (Bacocalmine™ from SEDERMA, WO 99/40897) and sea whip extract, extracts of *Glycyrrhiza glabra*, of mulberry, of melaleuca (tea tree), of *Larrea divaricata*, of *Rabdosia rubescens*, of *euglena gracilis*, of *Fibraurea recisa Hirudinea*, of *Chaparral Sorghum*, of sun flower extract, of *Enantia chlorantha*, of *Mitracarpe* of *Spermacocea* genus, of *Buchu barosma*, of *Lawsonia inermis* L., of *Adiantium Capillus-Veneris* L., of *Chelidonium majus*, of *Luffa cylindrical*, of Japanese Mandarin (Citrus reticulata Blanco var. *unshiu*), of *Camelia sinensis*, of *Imperata cylindrical*, of *Glaucium Flavum*, of *Cupressus Sempervirens*, of *Polygonatum multiflorum*, of *loveyly-hemsleya*, of *Sambucus Nigra*, of *Phaseolus lunatus*, of *Centaurium*, of *Macrocystis Pyrifera*, of *Turnera Diffusa*, of *Anemarrhena asphodeloides*, of *Portulaca pilosa*, of *Humulus lupulus*, of *Globularia cordifolia*, of *Coffea Arabica* and of *Ilex Paraguariensis*.

Extraction from the plant may be performed using conventional engineering such as phenolic extraction, from any part of the plant such as the flower, seed, fruit, root, tubercle, leaf, pericarp and preferably rhizome. The extraction solvents may be selected from amongst water, propylene glycol, butylene glycol, glycerin, PEG-6 caprylic/capric glycerides, polyethylene glycol, methyl and/or ethyl esters, diglycols, cyclical polyols, ethoxylated or propoxylated diglycols, alcohols (methanol, ethanol, propanol, and butanol) or any mixture of these solvents. Plant extracts according to the present invention may also be obtained by other processes such as maceration, simple decoction, lixiviation, reflux extraction, supercritical extraction with $CO_2$, ultrasound or microwave extraction or counter-current techniques, or by plant cell culture engineerings and/or fermentation. This list is not restrictive.

Suitable peptides can include, but are not limited to, di-, tri-, tetra-, penta-, and hexa-peptides and derivatives thereof. In one embodiment, the composition comprises from about $1 \times 10^{-7}$% to about 20%, more preferably from about $1 \times 10^{-6}$% to about 10%, even more preferably from about $1 \times 10^{-5}$% to about 5%, by weight of additional peptide.

As used herein, "peptide" refers to peptides containing ten or fewer amino acids and their derivatives, in particular acyl derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides.

Suitable dipeptides for use herein include but are not limited to Carnosine (beta-AH), YR, VW, NF, DF, KT, KC, CK, KP, KK or TT. Suitable tripeptides for use herein include, but are not limited to RKR, HGG, GHK, GKH, GGH, GHG, KFK, GKH, KPK, KMOK, KMO2K or KAvaK. Suitable tetrapeptides for use herein include but are not limited to RSRK (SEQ ID NO: 5), GQPR (SEQ ID NO: 6) or KTFK (SEQ ID NO: 7). Suitable pentapeptides include, but are not limited to KTTKS (SEQ ID NO: 4). Suitable hexapeptides include but are not limited to GKTTKS (SEQ ID NO: 8), VGVAPG (SEQ ID NO: 9) and of the type disclosed in FR 2854897 and US 2004/0120918.

Other suitable peptides for use herein include, but are not limited to lipophilic derivatives of peptides, preferably palmitoyl derivatives, and metal complexes of the aforementioned (e.g., copper complex of the tripeptide His-Gly-Gly). Preferred dipeptide derivatives include N-Palmitoyl-beta-Ala-His, N-Acetyl-Tyr-Arg-hexadecylester (CALMOSENSINE™ from SEDERMA, France, WO 9807744, U.S. Pat. No. 6,372,717). Preferred tripeptide derivatives include N-Palmitoyl-Gly-Lys-His, (Pal-GKH from SEDERMA, France, WO 0040611), Pal-KMO$_2$K, a copper derivative of His-Gly-Gly sold commercially as lamin, from Sigma, lipospondin (N-Elaidoyl-Lys-Phe-Lys) and its analogs of conservative substitution, N-Acetyl-Arg-Lys-Arg-NH$_2$ (Peptide CK+), N-Biot-Gly-His-Lys (N-Biot-GHK from SEDERMA, WO0058347) and derivatives thereof. Suitable tetrapeptide derivatives for use herein include, but are not limited to N-palmitoyl-Gly-Gln-Pro-Arg (SEQ ID NO: 3) (from SEDERMA, France), suitable pentapeptide derivatives for use herein include, but are not limited to N-Palmitoyl-Lys-Thr-Thr-Lys-Ser (SEQ ID NO: 2) (available as MATRIXYL™ from SEDERMA, France, WO 0015188 and U.S. Pat. No. 6,620,419) N-Palmitoyl-Tyr-Gly-Gly-Phe-X with X Met (SEQ ID NO: 10) or Leu (SEQ ID NO: 11) or mixtures thereof. Suitable hexapeptide derivatives for use herein include, but are not limited to N-Palmitoyl-Val-Gly-Val-Ala-Pro-Gly (SEQ ID NO: 1) and derivatives thereof.

The preferred compositions commercially available containing a tripeptide or a derivative include Biopeptide-CL™ by SEDERMA (WO0143701), Maxilip™ by SEDERMA (WO 0143701), Biobustyl™ by SEDERMA and MATRIXYL™ synthe'6™ (WO 2010/082175). The compositions commercially available preferred sources of tetrapeptides include RIGIN™ (WO0043417), EYELISS™ (WO03068141), MATRIXYL™ RELOADED, and MATRIXYL 3000™ which contain between 50 and 500 ppm of Palmitoyl-Gly-Gln-Pro-Arg (SEQ ID NO: 3), and carrier, proposed by SEDERMA, France (US2004/0132667).

The following marketed peptides can be mentioned as well as additional active ingredients: Vialox™, Syn-ake™ or Syn-Coll™ (Pentapharm), Hydroxyprolisilane CN™ (Exsymol), Argireline™, Leuphasyl™, Aldenine™, Trylgen™, Eyeseryl™, Serilesine™ or Decorinyl™ (Lipotec), Collaxyl™ or Quintescine™ (Vincience), BONT-L-Peptide™ (Infinitec Activos), Cytokinol™ LS (Laboratoires Serobiologiques/Cognis), Kollaren™, IP2000™ or Meliprene™ (Institut Europeen de Biologie Cellulaire), Neutrazen™ (Innovations), ECM-Protect™ (Atrium Innovations), Timp-Peptide™ or ECM Moduline™ (Infinitec Activos).

Composition Preparation

Compositions of the present invention comprising the GGP are generally prepared by conventional methods such as are known in the art of making topical and oral compositions and compositions for injection. Such methods can typically be conducted in one or more steps, with or without heating, cooling, and the like.

The physical form of the compositions according to the invention is not important: they may be in any galenic form such creams, lotions, milk or cream ointments, gels, emulsions, dispersions, solutions, suspensions, cleansers, foundations, anhydrous preparations (sticks, in particular lip balm, body and bath oils), shower and bath gels, shampoos and scalp treatment lotions, cream or lotion for care of skin or hair, make-up removing lotions or creams, sun-screen lotions, milks or creams, artificial suntan lotions, creams or milks, pre-shave, shave or aftershave creams, foams, gels or lotions, make-up, lipsticks, mascaras or nail varnishes, skin "essences," serums, adhesive or absorbent materials, transdermal patches, or powders, emollient lotion, milk or cream, sprays, oils for the body and the bath, foundation tint bases, pomade, emulsion, colloid, compact or solid suspension, pencil, sprayable or brossable formulation, blush, red, eyeliner, lip liner, lip gloss, facial or body powder, styling foams or gels, nail conditioner, lip balms, skin conditioners, moisturizers, hair sprays, soaps, body exfoliants, astringents, depilatories and permanent waving solutions, antidandruff formulations, anti-sweat and antiperspirant compositions, nose sprays and so on. These compositions can also be presented in the form of lipsticks intended to apply color or to protect the lips from cracking, or of make-up products for the eyes or tints and tint bases for the face. Compositions in accordance with the invention include cosmetics, personal care products and pharmaceutical preparations. The present invention may also be applied on animal skin and/or appendages. One can also consider a composition in the shape of foam or in the form of compositions for aerosol also including a propellant agent under pressure.

Cosmetic compositions according to the invention may also be for orodental use, for example, toothpaste. In that case, the compositions may contain the usual adjuvants and additives for compositions for oral use and, in particular, surfactants, thickening agents, moisturizing agents, polishing agents such as silica, various active substances such as fluorides, particularly sodium fluoride, and, possibly, sweetening agents such as saccharin sodium.

The GGP compound according to the present invention may be in the form of solution, dispersion, emulsion, paste, or powder, individually or as a premix or in vehicles individually or as a premix in vectors such as macro-, micro-, or nanocapsules, macro-, micro- or, nanospheres, liposomes, oleosomes or chylomicrons, macro-, micro-, or nanoparticles or macro-, micro or nanosponges, spores or exines, micro or nano emulsions or adsorbed on organic polymer powders, talcs, bentonites, or other inorganic or organic supports.

The GGP compound according to the present invention may be used in any form whatsoever, in a form bound to or incorporated in or absorbed in or adsorbed on macro-, micro-, and nanoparticles, or macro-, micro-, and nanocapsules, for the treatment of textiles, natural or synthetic fibers, wools, and any materials that may be used for clothing or underwear for day or night intended to come into contact with the skin, handkerchiefs or cloths, to exert their cosmetic effect via this skin/textile contact and to permit continuous topical delivery.

Method of Topical Cosmetic Treatment

The present invention also concerns a topical method to improve the general condition of the skin and appendages involving topical application to the skin of an effective amount of GGP in a physiologically acceptable medium. According to the invention the action of the GGP is preventive and restorative. In particular, the method according to the invention is a method:

- To prevent and/or treat the signs of intrinsic and extrinsic skin aging; and/or
- To prevent and/or treat skin from oxidative stress and free radicals; and/or
- To prevent and/or treat wrinkles and fine lines; and/or
- To prevent and/or treat skin sagging and/or improve tone and/or firmness and/or elasticity and/suppleness of the skin; and/or
- To prevent and/or treat skin atrophy and/or improve the density of the dermis and epidermis; and/or
- To give or return volume to the dermis and epidermis; and/or
- To prevent and/or treat pigmentation disorders
- To lighten and/or brighten the skin; and/or
- To prevent and/or treat skin roughness; and/or
- To prevent and/or treat inflammatory states.

The GGP composition according to the invention may be applied locally onto areas of the face, lips, neck, neckline, hands, feet, head or body. One of the major advantages of the present invention resides in the ability whenever necessary or desirable to be able to apply local selective "gentle" treatments through this topical, non-invasive method of application. In the case of anti-wrinkle use for example it may be applied very locally using a syringe or micro-canula.

It is also possible, however, to consider a composition containing the GGP compound according to the invention intended to be injected subcutaneously.

According to other specific features the treatment method according to the invention can be combined with one or more other treatment methods targeting the skin such as luminotherapy, aromatherapy or heat treatments.

According to the invention, devices with several compartments or kits may be proposed to apply the method described above which may include for example and non-restrictively, a first compartment containing a composition comprising the GGP compound, and in a second compartment a composition containing another active ingredient and/or excipient, the compositions contained in the said first and second compartments in this case being considered to be a combination composition for simultaneous, separate or stepwise use in time, particularly in one of the treatment methods recited above.

EXAMPLES

The following examples describe and demonstrate various aspects within the scope of the present invention. The examples are only given for illustrative purposes and should not be considered to be restrictive to this invention. Additionally for illustrative purposes several cosmetic formulations will be described. These formulations are representative of but do not restrict the invention.

1/ Formulation of a Composition According to the Invention Forming an Active Ingredient, Raw Material for Cosmetic Formulation Industry The GGP compound of isoprene type according to the invention is preferably solubilized in a hydrophobic matrix (e.g. based on triglycerides) at a concentration typically of 2% w/w (by weight of the total weight of the composition, = 20 000 ppm) to form the active ingredient that can be used in the manufacture of cosmetic products (see below galenic examples of point 3/).

2/ Galenic

2/1. Anti-Ageing Fluid Cream

| Product | % | INCI name |
|---|---|---|
| Phase A | | |
| $H_2O$ | Qsp 100 | Water |
| Sorbate | 0.10 | Potassium Sorbate |
| MgSO4 | 0.70 | Magnesium Sulfate |
| Phase B | | |
| ABIL EM 90 | 3.00 | Cetyl PEG/PPG-10/1 Dimethicone |
| Phenoxyethanol | Qs | Phenoxyethanol |
| Syncrowax HRC | 1.00 | Tribehenin |
| Crodamol STS | 2.00 | PPG-3 Benzyl Ether Myristate |
| Parleam oil | 19.00 | Hydrogenated polyisobutene |
| Phase C | | |
| Formula comprising 2% w/w GGP in a hydrophobic matrix | 2.00 | |
| Phase D | | |
| Fragrance | 0.10 | Fragrance |

Protocol: Step 1: weigh phase A, heat. Step 2: mix phase B, heat, mix thoroughly. Step 3: extemporaneously, add phase C in phase B, mix thoroughly. Step 4: slowly add phase A to phase B+C while stirring. Step 5: then add phase D. Stir until cooling.

2/2. Anti-Aging Cream

| Product | % | INCI name |
|---|---|---|
| Phase A | | |
| $H_2O$ | Qsp 100 | Water |
| Ultrez 10 | 0.25 | Carbomer |
| Phase B | | |
| Butylene glycol | 2.00 | |
| Phenoxyethanol | Qs | Phenoxyethanol |
| Phase C | | |
| Brij S2/Volpo S2 | 0.40 | Steareth-2 |
| Brij S10/Volpo S 10 | 1.20 | Steareth-10 |
| Crodafos CES | 4.00 | Cetearyl alcohol & Dicetyl Phosphate & Ceteth-10 Phosphate |
| Crodacol CS 90 | 0.50 | Cetearyl Alcohol |
| Laurocapram | 2.50 | Laurocapram |
| DC 345 | 2.00 | Cyclopentasiloxane & Cyclohexasiloxane |
| Crodamol OSU | 7.00 | Diethylhexyl succinate |
| Phase D | | |
| Formula comprising 2% w/w GGP in a hydrophobic matrix | 2.00 | |
| Phase E | | |
| Potassium sorbate | 0.10 | Potassium Sorbate |
| Phase F | | |
| $H_2O$ | 3.00 | Water |
| NaOH 30% | 0.40 | Sodium Hydroxide |

Protocol: Step 1: Weigh phase A and let swallow without stiffing. Step 2: Heat phase A in a water bath. Step 3: Weigh Phase B and mix. Step 4: Then add phase B into phase A in a hot water bath. Step 5: Weigh phase C and heat in a water bath. Mix thoroughly. Step 6: Add phase D to phase C, extemporaneously. Step 7: While stiffing pour phase C+D in phase A+B. Mix thoroughly. Step 8: Then add phase E, mix thoroughly. Step 9: Then add phase F, mix thoroughly until cooled.

2/3. Mattifying and Anti-aging Thick Cream

Combination of the GGP active ingredient according to the invention and the commercial mattifying ingredient EVERMAT® ™ (marketed by SEDERMA (WO 2007/029187)), which has a matt effect through action on the secretion of sebum.

| Product | % | INCI name |
|---|---|---|
| Phase A | | |
| $H_2O$ | Qsp 100 | Water |
| Optasens G83 | 0.35 | Carbomer |
| Phase B | | |
| Butylene Glycol | 2.00 | Butylene Glycol |
| Glycerin | 1.00 | Glycerin |
| Phenoxyethanol | Qs | Phenoxyethanol |
| Phase C | | |
| Crodamol AB | 4.00 | C12-15 Alkyl Benzoate |
| Optasens G82 | 0.25 | Acrylic acid/ alkylmethacrylate copolymer |

-continued

| Product | % | INCI name |
|---|---|---|
| Cromollient DP3A | 0.50 | PPG-3 Myristyl Ether Adipate |
| Estol 3609 | 1.00 | Triethylhexanoin |
| Formula comprising 2% w/w GGP in a hydrophobic matrix | 1.5 | |
| Phase D | | |
| Sorbate | 0.10 | Potassium sorbate |
| Phase E | | |
| NaOH 30% | 0.55 | Sodium hydroxide |
| H$_2$O | 5.00 | Water |
| Phase F | | |
| EVERMAT ® | 3.00 | Butylene Glycol (and) Enantia Chlorantha Extract (and) Oleanolic Acid |
| Phase G | | |
| Fragrance | 0.10 | Fragrance |

Protocol: Step 1: Phase A, sprinkle G83 Optasens in water, let swallow. Step 2: Weigh and mix phase B. Step 3: Add phase B into phase A under stirring. Step 4: Weigh phase C and mix. Step 5: Add phase C in phase A+B under stiffing. Step 6: Add phase D, mix thoroughly. Step 7: Add phase E, mix thoroughly. Step 8: Add phase F, mix thoroughly. Step 9: Finally add phase G, mix thoroughly.

2/4. Serum Form without Alcohol

| Product | % | INCI name |
|---|---|---|
| Phase A | | |
| H$_2$O | Qsp 100 | Water |
| Optasense G83 | 0.20 | Carbomer |
| Phase B | | |
| Glycerin | 5.00 | Glycerin |
| Phenoxyethanol | Qs | Phenoxyethanol |
| Phase C | | |
| Formula comprising 2% w/w GGP in a hydrophobic matrix | 2.00 | |
| Optasense G82 | 0.20 | Acrylic acid/ Alkylmethacrylate copolymer |
| Phase D | | |
| Potassium sorbate | 0.10 | Potassium Sorbate |
| Phase E | | |
| H$_2$O | 4.00 | Water |
| NaOH 30% | 0.40 | Sodium hydroxide |
| Phase F | | |
| Fragrance | 0.10 | Fragrance |

Protocol: Step 1: Phase A, sprinkle the carbomer in water, let swallow. Step 2: Weigh and mix phase B. Step 3: Add phase B to phase A while stiffing. Step 4: Weigh phase C and mix. Step 5: Add phase C to phase A+B. Mix thoroughly under stirring. Step 6: Weigh phase D. Step 7: Extemporaneously pour phase D into phase A+B+C, under stiffing. Step 8: Neutralize with phase E at room temperature. Step 9: Add phase F, homogenize. Check the final pH.

2/5. Soothing and Firming Gel/Cream Form

Combination of the GGP active ingredient according to the invention and the commercial ingredient IDEALIFT®™ which has a soothing and firming effect (comprising the lipo-dipeptide TyrArg marketed by SEDERMA (FR09/53444)).

| Product | % | INCI name |
|---|---|---|
| Phase A | | |
| Optasens G83 | 0.15 | Carbomer |
| H$_2$O | qsp 100 | Water |
| Phase B | | |
| Phenoxyethanol | Qs | Phenoxyethanol |
| Glycerin | 3.50 | Glycerin |
| Phase C | | |
| Optasens G82 | 0.20 | Acrylic acid/Alkylmethacrylate Copolymer |
| Polawax GP 200 | 1.00 | Cetearyl Alcohol & polysorbate 20 |
| Crodacol CS 90 | 1.00 | Cetearyl Alcohol |
| Crodamol STS | 1.00 | PPG-3 Benzyl Ether Myristate |
| DC 200 5 cps | 2.50 | Dimethicone |
| Crodamol TN | 1.50 | Isotridecyl Isononanoate |
| Phase D | | |
| Formula comprising 2% w/w GGP in a hydrophobic matrix | 2.00 | — |
| Phase E | | |
| Idealift ® ™ | 4.00 | Butylene Glycol - Water - Sorbitan Laurate - Hydroxyethylcellulose - Acetyl Dipeptide-1 Cetyl Ester - |
| Phase F | | |
| Potassium sorbate | 0.10 | Potassium Sorbate |
| Phase G | | |
| NaOH 30% | 0.20 | Sodium hydroxide |
| H$_2$O | 2.00 | Water |
| Phase H | | |
| Fragrance | 0.10 | Fragrance |

Protocol: Step 1: Disperse the carbomer in water without stirring. Let swallow. Step 2: Mix phase B. Step 3: Pour phase B in phase A, homogenize, heat using a water bath. Step 4: Weigh phase C, mix and heat using the water bath. Step 5: Add phase E in phase A+B. Step 6: Add phase D in phase C. Step 7: Add phase C+D into phase A+B+E under stirring. Step 8: Then add phase F in the previous phase under stiffing. Allow homogenize. Step 9: Neutralize with phase G while stirring at hot. Step 10: Then add phase H at hot, mix thoroughly. Step 11: Check the pH around 6.

2/6. Fluid Cream Form

Combination of the GGP active ingredient according to the invention and the commercial ingredient O.D.A. White®™ (marketed by SEDERMA (WO 94/07837)) which lightens the skin by reduction of melanin synthesis.

| Product | % | INCI name |
|---|---|---|
| Phase A | | |
| H$_2$O | Qsp 100 | Water |
| Potassium sorbate | 0.10 | Potassium Sorbate |
| Phase B | | |
| Keltrol CG-T | 0.60 | Xanthan Gum |
| Glycerin | 4.00 | Glycerin |
| Phenoxyethanol | Qs | Phenoxyethanol |

-continued

| Product | % | INCI name |
|---|---|---|
| Phase C | | |
| Brij S 721 | 5.00 | Steareth-21 |
| Brij S2/Volpo S2 | 1.00 | Steareth-2 |
| Prisorine 2034 | 7.50 | Propylene Glycol Isostearate |
| Estol 3609/Crodamol GTEH | 1.50 | Triethylhexanoin |
| O.D.A. white ® ™ | 1.00 | Octadecenedioic Acid |
| Phase D | | |
| Formula comprising 2% w/w GGP in a hydrophobic matrix | 2.00 | |
| Phase E | | |
| Perfume | 0.10 | Fragrance |

Protocol: Step 1: Weigh the phase A. Step 2: Weigh phase B and mix. Step 3: Add phase B into phase A under stirring, allow dispersing for 1 hour. Step 4: Heat phase A+B using a water bath. Step 5: Weigh phase C and heat using a water bath. Step 6: Weigh phase D, add in phase C. Step 7: Add phase C+D in phase A+B under stiffing. Step 8: Add phase E below 35° C., mix thoroughly. Step 9: Check pH, natural pH.

2/7. Face Cream Form

Ingredient composition according to the invention: formula comprising 2% w/w GGP in a hydrophobic matrix.

Examples of Other Additional/Optional Active Ingredients

Niacinamide (vitamine B3), Retinol, Resveratrol, DHEA: anti-aging actives, in particular anti-wrinkles.

Tocopherol or vitamine E, α-lipoic acid: anti-oxidant and anti-free radical properties Hexamidine: anti-microbial

| Cream form for the face | | % in weight | | | | | | |
|---|---|---|---|---|---|---|---|---|
| Ingredients | INCI name | n° 1 | n° 2 | n° 3 | n° 4 | n° 5 | n° 6 | n° 7 |
| Phase A | | | | | | | | |
| H₂O | Water | qsp100 | qsp100 | qsp100 | qsp100 | qsp100 | qsp100 | qsp100 |
| Ultrez 10 | Carbomer | 0.40 | 0.40 | 0.40 | 0.40 | 0.40 | 0.40 | 0.40 |
| Phase B | | | | | | | | |
| Glycerin | Glycerin | 3.00 | 3.00 | 3.00 | 3.00 | 3.00 | 3.00 | 3.00 |
| Panstat | Ethyl & Methyl & Propyl parabens | 0.30 | 0.30 | 0.30 | 0.30 | 0.30 | 0.30 | 0.30 |
| Phase C | | | | | | | | |
| Polawax GP 200 | Cetearyl Alcohol & polysorbate | 1.00 | 1.00 | 1.00 | 1.00 | 1.00 | 1.00 | 1.00 |
| Crodacol CS 90 | Cetearyl Alcohol | 1.00 | 1.00 | 1.00 | 1.00 | 1.00 | 1.00 | 1.00 |
| Crodamol STS | PPG-3 Benzyl Ether Myristate | 1.00 | 1.00 | 1.00 | 1.00 | 1.00 | 1.00 | 1.00 |
| DC 200 5 cps | Dimethicone | 2.50 | 2.50 | 2.50 | 2.50 | 2.50 | 2.50 | 2.50 |
| Crodamol TN | Isotridecyl Isononanoate | 5.00 | 5.00 | 5.00 | 5.00 | 5.00 | 5.00 | 5.00 |
| Phase D | | | | | | | | |
| Formula comprising 2% w/w GGP in a hydrophobic matrix | | 4.00 | 3.00 | 3.00 | 3.00 | 3.00 | 3.00 | 3.00 |
| Retinol | | | | | | | 0.1 | |
| Resveratrol | | | | | | | | 0.5 |
| Tocopherol | | 0.5 | | | | | | |
| α-lipoic acid | | | | | 0.2 | | | |
| DHEA | | | | | | 0.4 | | |
| Phase E | | | | | | | | |
| Sorbate | Potassium sorbate | 0.10 | 0.10 | 0.10 | 0.10 | 0.10 | 0.10 | 0.10 |
| Phase F | | | | | | | | |
| NaOH 30% | Sodium hydroxide | 0.40 | 0.40 | 0.40 | 0.40 | 0.40 | 0.40 | 0.40 |
| H₂O | Water | 4.00 | 4.00 | 4.00 | 4.00 | 4.00 | 4.00 | 4.00 |
| Phase G | | | | | | | | |
| Niacinamide 10% in water | | | | | | 10.00 | | |
| Hexamidine | | | 0.5 | | | | | |

-continued

| Cream form for the face | | % in weight | | | | | | |
|---|---|---|---|---|---|---|---|---|
| Ingredients | INCI name | n° 1 | n° 2 | n° 3 | n° 4 | n° 5 | n° 6 | n° 7 |
| Phase H | | | | | | | | |
| Fragrance | Fragrance | 0.10 | 0.10 | 0.10 | 0.10 | 0.10 | 0.10 | 0.10 |

Protocol: Step 1: Weigh phase A and let swallow for 30 minutes. Then heat at 75 C.° using a water bath. Step 2: Heat phase B until dissolution. Add phase B into Phase A. Step 3: Heat phase C in a water bath at 75 C.°. While stirring, add phase C to phase A+B. Step 4: Extemporaneously add phase D. Step 5: Add phase E, mix thoroughly. Step 6: Neutralize with phase F around 55° C. Step 7: Add phase G, then phase H Phase, mix thoroughly.

Other galenical formulations are obviously possible depending on the desired application, including hair, makeup, etc.

3/In Vitro and In Vivo Cosmetic Activity Studies

The GGP compound of the invention (thereafter referred to as the GGP) has a number of remarkable effects/actions presented below.

A) Cell and Mitochondria Protection, in Particular Against Oxidative Stress

1) Antiradical Effect and Thus Antioxidant Effect of the GGP

Radical oxygen species (ROS) are produced during normal physiological processes such as breathing or the inflammatory response, but they can also cause serious cell damage involved in skin aging if produced in excessive amounts (oxidative stress), then overwhelming the anti-oxidant defense mechanisms. Thus, the presence of antiradical compounds is interesting in cosmetic compositions in general, and even higher in anti-aging compositions.

Principle: the ORAC test ("Oxygen-Radical Absorbance Capacity") measures degradation by the oxidative way of a fluorescent molecule (fluorescein). Degradation of fluorescein by peroxyl radicals generated by AAPH (2,2'-azobis (2-amidinopropane) dichloride) induces a decrease in fluorescence measured by a spectrofluorometer during a degradation kinetic.

An antioxidant protects this fluorescein against this radical degradation. The decrease in fluorescence will be smaller and slower in the presence of the antioxidant than in its absence. The comparison between the parameters of the two kinetics makes it possible to calculate a percentage of protection against free radical degradation.

TABLE 1

Effect of the GGP on fluorescein degradation by peroxil radicals (n = 6)

| | Control | GGP 10 ppm | GGP 50 ppm | GGP 200 ppm | GGP 400 ppm |
|---|---|---|---|---|---|
| % of protection | Ref | 56% | 68% | 77% | 87% |
| Student t test | | $p < 0.01$ | $p < 0.01$ | $p < 0.01$ | $p < 0.01$ |

Positive control = Trolox 10μ = 94% ($p < 0.01$)

A significant and dose-dependent protection against the peroxyl radicals in the presence of GGP is observed.

2) Protection of Membrane Lipids by GGP

In the skin, a favorite target of oxygen free radicals is the unsaturated lipid, which is thus for the cosmetic industry a good study model for research of anti-radical compounds.

Principle: Cell membranes are composed of oxidable phospholipids. Using a cell-free model (unsaturated phospholipids based liposomes) and a reproducible oxidative stress (UVA radiation), it is possible to follow spectrophotometrically (at 233 nm) the formation of early by-products of lipoperoxidation that are conjugated dienes. An anti-lipoperoxidant agent can reduce or even eliminate this phenomenon.

TABLE 2

Effect of GGP on lipidic peroxidation by UVA

| | Control | GGP 8 ppm | GGP 26 ppm | GGP 80 ppm |
|---|---|---|---|---|
| % of peroxidation inhibition | Ref | 14% | 24% | 75% |
| Student t test | | $p < 0.05$ | $p < 0.01$ | $p < 0.01$ |

Positive control = 58% of inhibition ($p < 0.01$)

A significant and dose-dependant inhibition of the lipidic peroxidation in the presence of the GGP is observed.

3) Protection of Cell Membranes by the GGP

The antiradical power of a compound on a cell model subjected to oxidative stress can also be evaluate by measuring malonaldehyde, one of the end products of lipid peroxidation. This compound is involved in the oxidation of membrane proteins and in particular the enzymes of the respiratory chain, very sensitive to oxidative stress, hence the interest to limit his production.

Principle: human fibroblasts are grown to confluence and then placed or not in contact with the GGP for 72 hours. Following this contact, the GGP is removed and the cells are exposed to oxidative stress (UVA). After a further incubation with or without the GGP, malonaldehyde (MDA) is determined by the TBARS method (Thiobarbituric Acid Reactive Substances) and the value obtained divided by the amount of cellular protein.

TABLE 3

Effect of the GGP of lipidic peroxidation of fibroblast cellular membranes

| | Conc. | MDA concentration in (nM/mg protein) | % Change | % Change |
|---|---|---|---|---|
| Stress-free control | — | 131 +/− 13 | Ref. | — |
| Post-stress control | — | 1104 +/− 36 | +746%; $p < 0.01$ | Ref. |
| GGP | 3 ppm | 881 +/− 36 | — | −20%; $p < 0.01$ |
| | 5 ppm | 727 +/− 39 | — | −34%; $p < 0.01$ |
| | 7 ppm | 515 +/− 11 | — | −53%; $p < 0.01$ |

A significant and dose-dependent inhibition of the formation of malonaldehyde, end product of lipid peroxidation, in human fibroblasts subjected to oxidative stress is observed in presence of the GGP.

4) Protection of the Oxidable Lipids of the Stratum Corneum Against Oxidative Stress Lipids of the stratum corneum are the primary targets of free radical aggressions. Thus, it seemed interesting to test the antiradical capacity of the GGP in ex vivo condition on extracts of stratum corneum from volunteers who applied for 2 months, on one arm a placebo cream and on the other arm the GGP cream (Formulation 2/2 in the examples given above). These extracts are stressed to oxidize lipids. A lower oxidation in skin extracts which were in contact with the GGP is seeked.

Principle: 13 volunteers have applied 2 times daily for 2 months in a randomized manner the cream containing 0.04% of GGP on one forearm. The placebo cream was applied controlateral. Each subject was therefore his own control. At T0 and T2, specimens of stratum corneum were taken on the 2 arms with 3 adhesive discs per aim, and for each disk 15 take off (saturation of the disk).

The disks were stored at $-20°$ C. until lipoperoxidation testing. After rapid thawing at room temperature, the 3 discs from the same arms were collected and sonicated in a suitable diluent, to take off and recover the maximum amount of stratum corneum samples. The resulting suspension was then stressed overnight at $45°$ C., using a $H_2O_2/FeCl_2$ solution. The lipid peroxidation was assessed by measuring 8-isoprostanes (ELISA assay). The data were normalized using a protein assay.

In vivo, the 8-isoprostanes are non-enzymatically produced by a series of reactions catalyzed by free radicals. Any fatty acid having at least 3 double bonds may be the substrate of these reactions. Extracts of stratum corneum that were in contact with the GGP attained a level of protection against oxidation of +44% (p<0.05), compared with placebo extracts.

5) Cell Protection Against Oxidative Stress by the GGP

It is acknowledged that the senescence processus (stop of cell replication after a certain number of divisions) can be accelerated by treating the cells with sublethal concentrations of hydrogen peroxide (or other oxidizing agents). Specialists use the term "Stress Induced Premature Senescence" (SIPS) to describe this phenomenon.

One of the indicators conventionally used to assess the state of senescence of a cell population is the level of oxidative stress. This factor can be measured reliably thanks to a probe called DCFH-DA, whose characteristic is to fluoresce in contact with peroxides once it entered the cell. SIPS protocols and DCFH-DA probe as indicator of oxidative stress are thus commonly used in cosmetics for aging studies.

Principle: Fibroblasts at confluence contacted or not with the GGP for several days, are subjected to oxidative stress by hydrogen peroxide in the presence or absence of the GGP. This stress is intended to induce premature senescence in cells.

After this initial stress, the cells were detached from the support and returned to culture at low density until confluence. They are then contacted or not with the compound of the invention for 24 hours. At this stage, each set of cultures (with or without the tested compounds) is divided into 2 lots. A first batch (not stressed) is evaluated directly for its concentration of intracellular peroxides (using the probe DCFH-DA). Simultaneously, the other batch (stressed) undergoes a second stress by hydrogen peroxide (weaker than the first) just before being evaluated in the same way regarding the concentration of intracellular peroxides.

The amount of fluorescence measured with this probe is directly proportional to the amount of peroxides present in the cells.

Using this protocol with 2 inputs, the Applicant seeks two responses:

a) Does a prolonged contact with the GGP make the cells more resistant to SIPS (premature aging)?

b) Does the GGP make the cells that have undergone SIPS better resistant to an ulterior oxidative shock, less violent?

TABLE 4

Influence of the GGP on the intracellular peroxide level in FHN after a SIPS experiment.

| | Concentration | Endogen peroxides (UFA/million of cells) | % Change/ Control |
|---|---|---|---|
| Control | — | 101.6 +/− 7.7 | Ref. |
| GGP | 3 ppm | 61.2 +/− 2.6 | −40%; p < 0.01 |
| Trolox | 120 ppm | 57.5 +/− 3.8 | −43%; p < 0.01 |

A reduction of the peroxides induced by oxidative stress is obtained using the GGP at 3 ppm. The cells are thus protected against a major known cause of aging.

TABLE 5

Influence of GGP on the level of intracellular peroxides in prematurely aged fibroblasts (SIPS) and subjected to a second oxidant stress.

| | Concentration | Endogen peroxides (UFA/million of cells) | % Change/ Control |
|---|---|---|---|
| Control | — | 1053 +/− 56 | Ref. |
| GGP | 3 ppm | 161 +/− 14 | −85%; p < 0.01 |
| Trolox | 120 ppm | 158 +/− 7 | −85%; p < 0.01 |

The GGP provides to cells weakened by a first oxidative stress a significant and unexpected resistance against a second stress, less strong. At 3 ppm, it reduced by 85% the level of intracellular peroxides compared to control.

In all SIPS tests performed according to the scheme above, always more cells with the GGP at the tested concentrations (3 and 5 ppm) are obtained: between 25 and 50% of additional cells according to the tests compared to the control. This is conform to what is known about the action mode of the GGP. Indeed, as it contributes to the neutralization/elimination of the ROS, which in turn led to significant cellular damage, survival and growth of cells are best performed in the presence of GGP.

6) Mitochondrial Respiration Protection with the GGP

Mitochondrial respiration provides the ATP to cover the energy needs of the cell. The reduction of this ATP production is both a cause and a consequence of aging. An active that can counteract this decrease in ATP synthesis can therefore only have a beneficial and global effect against aging.

Principle: human dermal fibroblasts at confluence received the GGP for 24 h. After this phase, they were treated with hydrogen peroxide in the presence or absence of the GGP. This stress is intended to induce premature senescence (SIPS) in cells and thus a decrease in ATP synthesis. A few hours after this stress, cells were lysed and the amount of intracellular ATP was assessed by chemiluminescence. This amount of ATP was divided by the amount of intracellular proteins.

TABLE 6

Effect of the GGP on the quantity of ATP synthesized by fibroblasts in premature senescence after an oxidizing stress

|  | Conc. | ATP in nM/ 0.1 μg protein | Change (%) | Change (%) |
|---|---|---|---|---|
| Stress-free control | — | 1695 +/− 224 | Ref | |
| After-stress control | — | 177 +/− 93 | −90%; p < 0.01 | Ref |
| GGP | 5 ppm | 311 +/− 80 | — | +76%; p < 0.01 |
|  | 7 ppm | 988 +/− 38 | — | +460%; p < 0.01 |

The GGP can limit, significantly and dose-dependently, the depletion of ATP production induced by oxidative stress. It can therefore effectively protect the mitochondria's main function, which is the production of ATP, against a major cause of aging: the oxidative stress.

7) Protection of the Mitochondrial Membrane Potential by the GGP

The mitochondrial membrane potential (ΔΨ) obtained with a gradient of protons enables the formation of ATP at the level of the respiratory complexes. Its decrease causes a reduction of the formed ATP. The membrane potential is known to decrease with age (senescence). It also decreases in cell culture, following oxidative stress (SIPS), as in the course of a culture aging spontaneously (without SIPS). It is therefore a good senescence marker.

It is possible to measure the membrane potential through a specific membrane dye. Depending on the level of the membrane potential, this dye is rather present as monomer (emission fluorescence at 520 nm) or rather in the multimetric form (fluorescence emission at 590 nm). High membrane potential promotes a multimetric form.

The ratio λ520/λ590 varies inversely with the membrane potential. The lower the ratio is, the higher the membrane potential is. The increase in the ratio thus reflects a decrease in membrane potential. The ratio λ520/λ590 for young and proliferating cells is 2.97+/−0.17.

Principle: low proliferative cells were cultured for one week, in contact or not with the GGP at 3 and 5 ppm. After this period, the membrane potential of half of the cultures was measured.

TABLE 7

Effect of the GGP on the membrane potential of presenescent fibroblasts

|  | Concentration | ΔΨ loss * | % of protection of the respiration potential |
|---|---|---|---|
| Control | — | 1.43 +/− 0.29 | Ref. |
| GGP | 3 ppm | 1.11 +/− 0.33 | +22%; nsd |
|  | 5 ppm | 0.84 +/− 0.08 | +41%; p < 0.01 |
| Trolox | 120 ppm | 0.80 +/− 0.52 | +44%; nsd |

* with regard to non stressed young cells/nsd: non significant data

The GGP at 3 and 5 ppm protects the mitochondrial membrane potential of a culture of presenescents fibroblasts.

The other half of the cultures underwent an oxidative stress (hydrogen peroxide) before measuring their membrane potential.

TABLE 8

Effect of the GGP on the membrane potential of presenescent fibroblasts having undergone an oxidative stress

| With stress | Conc. | ΔΨ loss * | Change * | Improvement of the respiration potential |
|---|---|---|---|---|
| Control | — | 5.50 +/− 0.81 | −100% | 0% |
| GGP | 3 ppm | 3.57 +/− 0.69 | −65% | +35%; p < 0.05 |
|  | 5 ppm | 2.03 +/− 0.69 | −37% | +63%; p < 0.01 |
| Trolox | 120 ppm | 3.18 +/− 1.16 | −57% | +43%; p < 0.05 |

* with regard to non stressed young cells

The GGP at 3 and 5 ppm protects the mitochondrial membrane potential of a culture of fibroblasts against an oxidative stress.

B) Anti-Aging Influences, Preventive, Delaying the Apparition of Aging Signs

1) Effect of the GGP on the Telomere Length

Chromosomes, made up of DNA, have at their ends highly repetitive noncoding regions called telomeres. Telomeres have a protective role of the chromosome ends. In humans, telomeres are sequences of 3-20 kb with repetitions of the motif TTAGGG. As to the divisions, the telomere is not fully copied and therefore shortens this being not repairable in normal somatic cells. In cell culture, when telomeres have shortened sufficiently, cell division is no longer possible, the cell enters in senescence. This is true also in vivo, in the organism, where the shortening of telomeres with age has been observed in all somatic cells examined.

Thus, telomere length is a good marker of biological age of cells, and therefore the cosmetic industry is looking for compounds able to limit the shortening of telomeres, to delay aging.

The applicant has performed the average length measurement of the telomeres of a culture by a rapid method using PCR (Polymerase Chain Reaction) real-time quantitative.

This method relies on the use of two oligonucleotide primers specific of the telomeric repeat sequence (TTAGGG) and thus capable of hybridizing themselves to each of the two complementary strands of telomeric DNA, and then able to be amplified during the PCR cycles proportionally to the average length of telomeres of the genomic DNA of a given culture. A fluorescent molecule, intercalated into DNA double strand, is used to quantify the phenomenon (hybridization+amplification) at the end of each cycle. The parameter for evaluating the significance of this phenomenon is the Ct, cycle number of hybridization amplification necessary to reach a given fluorescence threshold above background noise.

Each Ct will be converted into an average length of telomeres, with a reference range obtained with successive dilutions from a standard solution of a synthetic oligonucleotide of 84 bases, consisting of 14 repeats of the TTAGGG sequence, each of these dilutions (or point range) being subjected to real-time quantitative PCR.

To be accurate, the assessment must take into account the number of genomes present. The latter will be appreciated by a PCR conducted in parallel with a control gene, 36B4, encoding a ribosomal phosphoprotein with two primers (oligonucleotides) specific for this gene. The Ct obtained in this PCR will be converted into a number of genomes using a standard range made from an oligonucleotide of 75 bases, representing the amplicon obtained with primers specific to 36B4.

Therefore is obtained for each total DNA extracts from a given culture, an average length of telomere per genome.

For assessments conducted simultaneously, it is possible to compare these values and see for example the influence of a compound on the average telomere length per genome.

In a protocol of senescence (natural or induced), on cell layers that contacted the GGP a telomere average length by genome larger than in the control layers is seeked.

Principle: Normal human dermal fibroblasts are grown on several cell passages, in contact or not with the GGP until a strong slowdown and little or not proliferative cells. At this stage, cultures are stopped, DNA extracted and the average telomere length measured for each culture.

TABLE 9

Effect of the GGP on the mean length of fibroblast telomeres subjected to natural senescence (n = 3)

| | Conc. | Mean telomere length (in kb/genome) | Telomere erosion due to aging (in kb/genome) | % of protection against natural telomere erosion |
|---|---|---|---|---|
| Proliferative cells | — | — | 10.66 +/− 1.80 | Ref. |
| Presenecent cells (little or no proliferation) | Control | — | 6.90 +/− 0.44 | −3.76 kb; p < 0.05 | Ref |
| | GGP | 1.65 ppm | 8.35 +/− 0.75 | −2.31 kb; nsd | +1.45 kb → +38%; p < 0.05 |

This study shows that long-term culture of human dermal fibroblasts in the presence of GGP can protect cells against telomere shortening compared to the control. The percentage of protection is 38%.

2) Influence of the GGP on the Activity of β-Galactosidase Associated to Senescence An isoform of β-galactosidase with an optimum activity at pH 6 is expressed specifically during senescence ("Senescence Associated beta-gal or SA-beta-gal"). The accumulation of the enzyme occurs in the lysosomes of the cell. It is so far a widely used marker of cellular senescence. Its measurement can be done in two ways: by a colorimetric method or by a fluorimetric method. The Applicant has developed the fluorimetric method, which appeared both faster and more reliable.

In a protocol of senescence (spontaneous or induced), a lower level of expression of β-galactosidase on cell layers that had contacted the GGP compared to a control layer are seeked Principle: Proliferative human dermal fibroblasts were contacted or not with the GGP for 72 hours in a growth medium. After this first incubation, the cells were subjected for 5 days to an oxidative stress daily, one hour each, in a basic medium, common to all cultures. This stress is known to create a SIPS and to induce a strong increase in β-galactosidase activity in the stressed culture compared to an unstressed culture. Between two stress cells are returned to the growth medium with or without the substance tested. After the fifth stress, β-galactosidase activity is evaluated.

Evaluation of β-galactosidase activity is done after fixing the layers. They are put in contact with a substrate of β-galactosidase nonfluorescent FDG (fluorescein di-β-galactopyranoside), which will release a fluorescent compound upon hydrolysis by β-galactosidase. The emitted fluorescence is quantified in a fluorometer. It will increase with the amount of senescent cells present in culture. The relative activity of β-galactosidase thus found is 2974+/−957 UFA/million cells in a proliferative culture and increases by a factor 5 (p<0.01) in a culture little to not proliferative. The applicant has monitored in a cell-free system that the GGP was not an inhibitor of β-galactosidase

TABLE 10

Effect of the GGP on the expression level of β-galactosidase of presenescent fibroblasts after an oxidising stress (n = 4)

| | Concentration | Relative activity (FAU/$10^6$ cells) | Change with regard to control |
|---|---|---|---|
| Control | — | 5722 +/− 1419 | Ref. |
| GGP | 3 ppm | 3702 +/− 992 | −35%; p = 0.05 |
| | 5 ppm | 2789 +/− 803 | −51%; p < 0.02 |

Positive control: Trolox 120 ppm = −45% (p < 0.05)

The compound of the invention can reduce, significantly and dose-dependently, the β-galactosidase activity compared to the control. It protects human dermal fibroblasts efficiently against aging-induced by an oxidative stress.

C) Improvement of Dermal Matrix Synthesis and of its Contractile Abilities

1) Influence of the GGP on Collagen I Synthesis by Human Dermal Fibroblasts

Within the dermis, the fibroblasts produce collagen I in the form of monomers, which are subsequently assembled into fibers in the extracellular matrix.

One consequence of skin aging in the dermis is the decrease of collagen synthesis (1% per year from age 20). It partly explains the gradual decrease of the thickness, firmness and elasticity of the skin over time. For this reason, the interest of stimulating the collagen synthesis in fibroblasts to slow skin aging is now recognized Principle: The collagen I synthesis was monitored in presenescent human dermal fibroblasts. These cells were cultured for 11 days with the GGP in a growth medium. Following this incubation, the cell layers were fixed and labeled by immunofluorescence, to visualize the network of collagen I and to quantify by image analysis on photographs. In parallel, quantification was performed on proliferating cells.

TABLE 11

Effect of GGP collagen I synthesis in presenescent fibroblast (n = 20 photos/case)

|  | Concentration | UFA/ $10^4$ cell | Change (%) |  |
|---|---|---|---|---|
| Proliferative cells | — | 230 +/− 200 | Ref |  |
| Senescent cells | — | 60 +/− 70 | −74%; $p < 0.01$ | Ref. |
| Senescent cells + GGP | 3 ppm | 280 +/− 220 | +367%; $p < 0.01$ |  |
|  | 5 ppm | 350 +/− 290 | +483%; $p < 0.01$ |  |

Positive control: TGF-β at $10^{-6}$%: ×8.3 times

The compound of the invention enables in presenescent fibroblasts an important and dose-dependent stimulation of collagen I synthesis compared to control. The level of synthesis obtained is even higher than that observed for proliferative cells. These results confirm what is obtained on proliferative cells: GGP activates collagen synthesis to a level close to that observed above, compared to control.

GGP, by stimulating the collagen I synthesis, slows the loss of elasticity of the skin during aging. An ex vivo test done on skin explants confirmed this protective effect. A cream containing 0.04% of GGP was applied to them 2 times daily for 5 days. Control skin explants received a placebo cream in parallel. Following these applications, the skins were cutted and labeled with anti-collagen I fluorescent antibodies. Photographs of sections were made and quantified by fluorescence. This gives a stimulation of the synthesis of +14% ($p<0.05$) with the GGP. By the same technique, an increase of the lysyl hydroxylase (+13%, $p<0.05$) was measured with a cream containing 0.04% of GGP compared with a placebo cream. This result can be put in parallel to results of a DNA array that show increased expression of two genes controlling the synthesis of the enzyme lysyl hydroxylase PLOD2 and JMJD6 on fibroblasts after 6 and 24 hours of contact with the GGP. These genes are involved in the hydroxylation of lysine residues in collagen molecule. This hydroxylation is involved in the stabilization of intra- and inter-molecular covalent bonds in collagen fibers.

2) Effect of the GGP on the Hyaluronic Acid Synthesis by Human Dermal Fibroblasts Hyaluronic acid is one of the main constituents of the dermis and epidermis. It has a very large capacity to capture and retain water. With age, the skin loses hyaluronic acid (−50% between age 20 and 50), resulting in dry skin and wrinkles. By stimulating the hyaluronic acid synthesis, dermis hydration and elasticity are increased.

In addition, through its ability to uptake water, hyaluronic restores back volume to the emaciated skins and can refills wrinkles and fine lines.

Principle: Human dermal fibroblasts were grown in plate for 24 hours. The cells are then placed in contact or not with GGP for 24 hours. Culture supernatants were collected and assayed for the amount of hyaluronic acid (HA) is then divided by the number of cells present on the layer. TGF-β1 is used as a positive control.

TABLE 12

Effect of GGP on the hyaluronic acid synthesis in human fibroblasts (n = 5)

|  | Concentration | ng of AH/ $10^6$ cells | % of change | Significance |
|---|---|---|---|---|
| Control | — | 4327 +/− 382 | Reference |  |
| GGP | 3 ppm | 5322 +/− 157 | +23% | $p < 0.01$ |
|  | 5 ppm | 5758 +/− 82 | +33% | $p < 0.01$ |
|  | 7 ppm | 6101 +/− 320 | +41% | $p < 0.01$ |
|  | 10 ppm | 6331 +/− 365 | +46% | $p < 0.01$ |

Positive control: TGF-β1 à $10^{-6}$%: +206% ($p < 0.01$)

The GGP stimulates the synthesis of hyaluronic acid in the human fibroblast in a dose-dependent manner. By this action, it will slow skin drying. This result is supported and confirmed by that of a DNA array which shows an increase in gene expression of hyaluronic acid synthase 2 on fibroblasts after 3, 6 and 24 hours of contact with the GGP.

3) Effect of the GGP on the Contractile Ability of Dermis

Aging results in a reduction of the viscoelastic properties of the skin, with a dermis more slackened and less contractile. At the cellular level, the senescent fibroblast has a wide and spread shape of different aspects compared to the fusiform young fibroblast. This morphological change is linked to intracellular cytoskeletal changes including reduced production of actin and disruption of its network. The formation of this network, made possible by the polymerization of actin, requires energy in the form of ATP, whose amount decreases with age. With fewer actin and fewer ATP, the cell will divide less. Moreover, the shape and the age of fibroblasts influence the mechanical properties of the dermis and its contractile capacity. Thus, the aged fibroblasts showing a reduced proliferative potential and a disruption of the actin network have a reduced ability to contract collagen gels. It is this last property that the applicant has used to show the efficiency of the GGP to reduce the senescent signs.

Principle: Proliferative human dermal fibroblasts were cultivated with or without the GGP over several generations to obtain presenescent cells. A constant number of cells from each case was then included in a collagen gel. The contractile capacity of cells was then followed by using photographs. Quantification by image analysis, focused on the intensity of the contraction (gel surface) and the contraction quality (gel heterogeneity).

TABLE 13

Effect of GGP on the ability of contracting a collagen gel of human dermal fibroblasts cultivated until presenescence of the controls (n = 5).

|  | Concentrations | Gel surface (cm$^2$) | % change; significance | Gel heterogeneity (UA) | % change; significance |
|---|---|---|---|---|---|
| Control | — | 7.42 ± 2.43 | Reference | 27.1 +/− 3.7 | Reference |
| GGP | 3 ppm | 6.12 ± 1.94 | −17.5%; $p < 0.01$ | 22.9 +/− 4.1 | +16%; nsd |
|  | 5 ppm | 5.82 ± 1.69 | −21.5%; $p < 0.01$ | 21.8 +/− 3.6 | +20%; $p < 0.02$ |

This study clearly shows that the pre-senescent fibroblasts have weak collagen contractile ability and provide gels with heterogeneous aspect.

The contact with GGP enabled the cells to limit the loss of their contractile ability, which results in a significantly lower gel surface compared to the control. In addition, the GGP provides a better contraction homogeneity; the dose-effect is a trend at 3 ppm (+16%) and significant at 5 ppm (+20%). This result is supported and confirmed by that of a DNA array which shows an increase in gene expression of actin gamma 2 (ACTG2) and of the "filament associated actin protein" (AFAP1L1) on fibroblasts after 3, 6 and 24 hours of contact with the GGP. These genes are involved in the cytoskeleton maintaining.

4) Influence of the GGP on the Decorin Synthesis by Human Dermal Fibroblasts

Decorin is a leucine-rich glycoprotein that participates in the assembly of the dermis by binding to collagen fibers and tropoelastin. The quality of this assemblage reflects the mechanical properties of the skin: elasticity, compressibility, strength. A stimulation of the synthesis of decorin is therefore seeked.

Principle: Normal human fibroblasts were brought to confluence, then contacted or not with GGP at 3, 5 or 7 ppm for 3 days. After this incubation, decorin content was assayed by ELISA in cell homogenates, and then divided by the number of cells.

TABLE 14

Influence of GGP on decorin biosynthesis by cells in a fibroblast culture (n = 5)

|  | Concentration | Decorin (pg/$10^6$ cell) | Change (%) |
|---|---|---|---|
| Control | — | 41366 +/− 3542 | Reference |
| GGP | 3 ppm | 47578 +/− 3587 | +15%; $p < 0.03$ |
|  | 5 ppm | 54419 +/− 4697 | +32%; $p < 0.01$ |
|  | 7 ppm | 58168 +/− 5912 | +41%; $p < 0.01$ |

There is a significant and dose-dependent synthesis of decorin by human fibroblast in the presence of GGP.

These effects on matrix synthesis associated with the results obtained on contraction, show that the GGP acts on fibroblasts in order to enhance the mechanical properties of the dermis.

5) Influence of the GGP on the Syndecan 1 Synthesis by Human Keratinocytes

Syndecan 1 is a small proteoglycan transmembran protein that is strongly implicated in keratinocyte activation and cohesion. The production of syndecan 1 diminishes with age resulting in a lack of cohesion at the level of epidermis (in the supra basal layers).

Principle: Human keratinocytes (NHK) are cultivated in a growth medium. After 6 days of incubation, the cells are contacted or not with the tested products (GGP and GGA) at 3, 5 or 7 ppm for 48 h. After incubation, the supernatants are taken and the syndecan 1 content is assayed by ELISA in these supernatants. The cell layers are sonicated and the cell number is evaluated by Hoechst method.

TABLE 15

GGP and GGA influence on syndecan 1 synthesis in NHK supernatants (n = 3)

|  | Concentration | Syndecan 1 (pg/$10^6$ cell) | Change (%) |
|---|---|---|---|
| Control | — | 69.1 +/− 2.0 | Reference |
| GGP | 3 ppm | 135.3 +/− 6.3 | +96%; $p < 0.01$ |
|  | 5 ppm | 200.6 +/− 15.8 | +190%; $p < 0.01$ |
|  | 7 ppm | 265.5 +/− 24.3 | +284%; $p < 0.01$ |
| Control | — | 136.0 +/− 10.0 | Reference |
| GGA | 3 ppm | 141.3 +/− 12.9 | +4%; nsd |
|  | 5 ppm | 155.7 +/− 14.4 | +14%; nsd |
|  | 7 ppm | 183.4 +/− 21.9 | +35%; $p < 0.05$ |

The results show that there is a significant and dose dependent stimulation of the synthesis of syndecan 1 in human keratinocyte in the presence of GGP (stimulation>200% in the presence of 7 ppm of GGP). Comparatively, the GGA presents a low stimulating activity of syndecan 1 syntesis (stimulation<50% in the presence of 7 ppm of GGA).

Therefore, GGP can boost the synthesis of syndecan 1 in keratinocytes to reinforce the skin cohesion.

D) Action on Pigmentation

The cosmetics industry is looking for compounds with depigmenting properties (bleaching, depigmentation and skin lightening, removing or attenuation of freckles, age spots etc . . . ). It is possible to demonstrate in vitro such an effect by measuring the melanin synthesized and the tyrosinase activity in cultured melanocytes having or not been in contact with the GGP.

Principle: Human melanocytes are seeded and placed in contact with the GGP for 5 days. After incubation, the residual tyrosinase activity and total melanin content were measured in cell homogenates, and then divided by the number of cells (melanin) or to the protein amount (tyrosinase).

TABLE 16

Influence of GGP on the tyrosinase activity and the melanin content on human melanocytes after 5 days of contact with the GGP (n = 4)

|  |  | Melanin | | Tyrosinase | |
|---|---|---|---|---|---|
|  | Conc. | Melanin content (µg/mL/$10^6$ cell) | Change (%) | tyrosinase activity (U/µg prot) | Change (%) |
| Control | — | 48.8 +/− 1.2 | Ref | 6.989 +/− 0.310 | Ref. |
| GGP | 1 ppm | 46.6 +/− 2.4 | −4%; nsd | 6.196 +/− 0.318 | −11%; $p < 0.05$ |

TABLE 16-continued

Influence of GGP on the tyrosinase activity and the melanin content on human melanocytes after 5 days of contact with the GGP (n = 4)

| | Melanin | | Tyrosinase | |
|---|---|---|---|---|
| Conc. | Melanin content (µg/mL/ $10^6$ cell) | Change (%) | tyrosinase activity (U/µg prot) | Change (%) |
| 3 ppm | 31.3 +/− 1.4 | −36%; $p < 0.01$ | 4.956 +/− 0.129 | −29%; $p < 0.01$ |
| 5 ppm | 20.2 +/− 1.3 | −59%; $p < 0.01$ | 3.588 +/− 0.248 | −49%; $p < 0.01$ |

Arbutine (positive control) 0.03%; −40%; $p < 0.01$ for melanin; −33%; $p < 0.01$ for tyrosinase There is a decrease of tyrosinase activity and melanin content, significant and dose dependent between 1 and 5 ppm of GGP.

E) Protective Effect on Epidermis

Keratinocyte Protection Against UVB Conferred By the GGP

The skin is very sensitive to UV radiation. Overexposure to the sun (which includes UV A and B in its spectrum) can lead to premature aging of the skin, even to cancer process. Thus, it is important for the cosmetic industry to find compounds able to counteract the negative effects of UV radiation and consequently to protect the skin against this aging factor.

Keratinocytes in monolayer, after an UVB radiation (12 to 240 mJ/$cm^2$), develop on their surface many burgeons, detach from the culture medium, undergo damages up to death. A cell count at various times after UVB radiation is used to evaluate the cell viability of the culture. This model is widely used in cosmetics to evaluate the protective effect of various compounds against the deleterious effects of UVB stress.

Principle: Keratinocytes were cultured in 35 mm dish. Just at confluence, the cells are contacted or not with the GGP for 24 hours. UVB irradiation (50 mJ/$cm^2$) is performed the next day, and the cells are or not contacted with the GGP. Six days later, the cells are counted to determine the cell viability in culture.

TABLE 17

GGP influence on the keratinocyte culture survival and recovery a UVB stress (n = 3).

| | | Cell number (×$10^5$)/35 mm dish | | | |
|---|---|---|---|---|---|
| | Conc. | mean (n = 3) | deviation | % change/ control | Statistic (t student) |
| Control | — | 3.68 | 0.44 | Ref. | Ref. |
| GGP | 1 ppm | 4.83 | 0.71 | +31% | $p < 0.05$ |
| GGP | 1.65 ppm | 5.08 | 0.56 | +38% | $p < 0.01$ |

The GGP, at 1 and 1.65 ppm, has a significant protective effect against the effects of UVB stress that manifests itself on the number of cells counted. Moreover, there is observed with a microscope, less damage to the cell layers and cells in better condition, in the presence of GGP F) Effect on the Dermo Epidermal Junction Action on Nidogen 1, which is a Molecule of the Dermo Epidermal Junction Nidogen 1 is a key component of the basement membrane. It stabilizes and strengthens it by linking laminin to collagen 4. We therefore seek to stimulate its synthesis.

Principle: Normal human fibroblasts were brought to confluence, then placed or not in contact with the GGP, at 1 or 2.5 ppm, for 3 days. After this incubation the nidogen 1 content is determined by ELISA in cell homogenates, and divided by the number of cells.

TABLE 18

Effect of GGP on the nidogen 1 biosynthesis by cell in a fibroblast culture (n = 5)

| | Control | GGP 1 ppm | GGP 2.5 ppm |
|---|---|---|---|
| Stimulation % | Reference | +28% | +94% |
| Test t student | | $p < 0.05$ | $p < 0.01$ |

There is a significant and dose-dependent synthesis nidogen 1 by human fibroblast in the presence of 1 and 2.5 ppm of GGP.

G) Anti-Aging Effects, Reducing the Signs of Aging, In Vivo Studies Principle

Two studies were conducted to evaluate the anti-aging efficacy of a composition comprising the GGP at 0.04% (formula 2/2 in the formulation examples given above):

A study addressed to the decrease in wrinkles and fine lines and included 28 female volunteers. During this study, the improvement of the viscoelastic parameters was monitored.

A study of the improvement of the appearance of the decollete (low necked); monitoring of the attenuation of the hollow of that area and decrease in the crumpled appearance (15 female subjects).

Several complementary methods were combined during these studies:

Wrinkles and fine lines: analysis of the crow's feet by fringe projection (FOITS), negative prints and standardized photographs.

Viscoelastic properties: analysis using the Aeroflexmeter™ (applicant patent applications FR2931651 and WO2009144680).

Folding of the skin of the decollete: analysis of the hollow, contour and folding of the decollete by fringe projection (FOITS) and standardized photographs.

Analysis of the dermal redensification of the decollete: by ultrasound echography.

Self-assessment of the effects by the volunteer or assessment by an expert panel.

Protocol

Particular Study Inclusion Criteria

Women with wrinkles in the crow's feet or the decollete were included. They were complied with a 15-day use of placebo before the beginning of the test (T0).

Hormonal consistency was required over the 3 months preceding the test and during the test (no change in contraceptive treatment, hormone-replacement or curative treatment).

Exclusive use of the cosmetic products supplied throughout the duration of the study was required.

Study Type and Duration

The clinical trials were conducted using a single-bind design and non-invasive methods. The trials addressed:

28 volunteers (mean age: 58.4 years [46 to 76 years]) who applied randomized the cream comprising 0.04% of GGP, either to half the face, either to a forearm. A control cream was applied contralaterally. Each subject acted as his own control.

15 volunteers (mean age: 57.8 years [46 to 69 years]) were selected for the decollete study. The subjects applied to the decollete the cream comprising 0.04% GGP. No placebo was used in the study since the decollete is not conducive to placebo use.

The 0.04% GGP cream or the control cream were applied twice daily by massage into the selected sites for 1 to 2 months.

The study is summarized in the flow chart provided herein as FIG. 1.

1) Facial Relief Study

Fringe projection The contact-free fast optical in vivo topometry system (FOITS) can be used to acquire the 3-D topography of the crow's foot by analysis of the deformation of the fringes projected on the skin. The system used (Dermatop; Breukman—Eotech) consists of a projector and camera which are associated forming a precise angle and enabling triangulation and 3D reconstruction of the relief An analysis is subsequently conducted using the <<Optoca>> program (Breukman—Eotech) in order to extract on one hand the volume occupied by the wrinkles and on the other hand the mean relief (roughness).

TABLE 19

Improvement of the profilometric parameters after application of GGP 0.04%
(Mean values for 25 volunteers, n = 1 measurement/volunteer).

|  | Volume occupied by the wrinkles (mm$^3$) | | Rugosity (nm) | |
| --- | --- | --- | --- | --- |
|  | T0 | T 2 months | T0 | T 2 months |
| Placebo cream | 5.00 +/− 3.23 | 4.95 +/− 2.79 | 105 +/− 40 | 103 +/− 40 |
| Change (%); significance |  | −1%; nsd |  | −2%; nsd |
| 0.04% GGP cream | 4.77 +/− 2.39 | 4.00 +/− 2.29 | 107 +/− 40 | 99 +/− 30 |
| Change (%); significance |  | −16.1%; $p < 0.05$ |  | −7.5%; $p < 0.04$ |
| Max |  | −35.4% |  | −60% |
| Significance vs. placebo |  | $p < 0.04$ |  | $p < 0.09$ |

After 2 months of application of the cream at 0.04% of GGP, there is an improvement, with a significant decrease in wrinkle volume of −16% (maximum −35%) associated with a significant decrease in roughness—7.5% (maximum −60%). Compared to placebo which undergoes little or no change, the effect is significant with $p<0.04$ for the volume and $p<0.09$ for the roughness.

Print analysis Standardized negative prints method using Silflo®™ on crow's feet of the volunteers was used. The prints were analyzed by an image analysis system using the projected-shadow method. The method consists in projecting a beam of light at a constant acute angle onto the print, thus generating shadows whose magnitude varies with the relief A specific analysis and surface representation enables quantification and representation of this relief.

In complement of the obtained results on a large surface with the FOITS, specific parameters of only one main wrinkle were extracted: depth and volume.

TABLE 20

Improvement in profilometric parameters after application of the 0.04% GGP cream (mean values for 27 volunteers, n = 1 measurement/volunteer).

| Volume of the main wrinkle (mm$^3$) | Placebo | | Creme GGP 0.04% | |
| --- | --- | --- | --- | --- |
|  | T0 | T1 m | T0 | T1 m |
| Mean | 0.243 +/− 0.144 | 0.254 +/− 0.146 | 0.251 +/− 0.173 | 0.196 +/− 0.089 |
| T1 m/T0 difference | +0.011 | | −0.055 | |
| Change (%) 1m vs. T0 (→ max) | 4.5%; nsd | | −22% ; $p < 0.01$ (→ −71%) | |
| Change (%) 0.04% GGP cream/placebo (→ max) | −26.4%; $p < 0.02$ | | | |

| Depth of the main wrinkle (μm) | Placebo | | 0.04% GGP cream | |
| --- | --- | --- | --- | --- |
|  | T0 | T1 m | T0 | T1 m |
| Mean | 88.18 +/− 29.99 | 91.71 +/− 29.92 | 92.53 +/− 29.97 | 76.90 +/− 23.93 |
| T1 m/T0 difference | +3.53 | | −15.63 | |

TABLE 20-continued

Improvement in profilometric parameters after application of the 0.04% GGP cream (mean values for 27 volunteers, n = 1 measurement/volunteer).

| Change (%) T1 m vs. T0 (→ max) | 4%; nsd | −16.9%; p < 0.01 (→ −57%) |
|---|---|---|
| Change (%) 0.04% GGP cream/placebo | | −21%; p < 0.01 |

With this method, a significant decrease in the depth and volume of the main wrinkle is observed as of 1 moth, whereas the placebo cream was devoid of effect. With regard to the volume of this main wrinkle, a significant decrease of 26% between the 2 sides is observed. In parallel, the depth of this wrinkle decreases very significantly of 21% between the 2 sides.

Standardized Photographs

Reproducible photographs were obtained using a digital photographic system consisting of a flash-lighting system and a subject-restraint system preventing movements of the head. The volunteer posture and the photographic and lighting parameters were standardized and controlled in order to ensure the reproducibilty over time.

An improvement of the relief of the crow's foot was observed between T0 and T2mnths with 0.04% GGP cream. Smoothing of the relief of the GGP treated zone is clearly observed. 2) Study of the Viscoelasticity on the Face The Aeroflexmeter™ is a system enabling the characterization of the viscoelastic properties of the skin without contact with the measurement zone. The system combines the projection of a laser-beam on the skin to a deformation of this skin area by a jet of compressed air. The deformation of the laser beam is very precisely recorded using the triangulation principle. With this system the 3-dimensional characteristics of the skin deformation can be measured. The density parameter was studied: D10, which is given by the angle made by the straight line intercepting the deformation curve at 10 and 50 depth. This angle represents the verticality of the deformation. With a young skin, which absorbs well the stress imparted by the compressed air, the angle is more acute, close to 0.degree., than for more elderly skin (wider angle, closer to) 90°).

TABLE 21

Improvement of the visco-elastic parameters after application of the 0.04% GGP cream (mean values for 23 volunteers, n = 5 measurements/volunteer).

| D10 (in d°) | Placebo | | 0.04% GGP cream | |
|---|---|---|---|---|
| | T0 | T2 m | T0 | T2 m |
| Mean | 10.73 +/− 3.46 | 10.80 +/− 4.05 | 9.85 +/− 2.88 | 8.69 +/− 1.96 |

TABLE 21-continued

Improvement of the visco-elastic parameters after application of the 0.04% GGP cream (mean values for 23 volunteers, n = 5 measurements/volunteer).

| D10 (in d°) | Placebo | | 0.04% GGP cream | |
|---|---|---|---|---|
| | T0 | T2 m | T0 | T2 m |
| T2 m/T0 difference | +0.07 | | −1.16 | |
| Change (%)* (* 100 × (T0 − T2 m)/ T0 T2 m vs. T0 (→ max) | −4%; nsd | | 11.8%; p < 0.01 (→ +37%) | |
| Change (%)0.04% GGP cream/ placebo | | +15.8%; p < 0.01 | | |

With the Aeroflexmeter™, an increase of almost 16% (with p<0.01) is observed on the side treated with 0.04% GGP cream compared to the placebo side. These results show that the skin is strengthened by the applications of the cream according to the invention: it better absorbs the stresses imparted.

3) Study of the Hollow, Curvature and Creasing of the Decollete

Fringe projection The method used is the same as disclosed in the above paragraph 1) (FOITS). The studied area is the hollow of the decollete (area between the breasts) which is often accentuated and fold with age. The selection of this area is assisted by a computer and enables to extract the same area at T0, T1month and T2months. From one acquisition, the volume and depth of the hollow were thus calculated. In addition, the curvature of the decollete was determined enabling the calculation of the radius of curvature. Due to the sagging and the folding, the radius of curvature tends to decrease in elderly women compared to younger women. A filling-out and increase in the density of the decollete leads to a decrease of the volume and depth of the hollow, and to an increase of the radius of curvature of the decollete.

TABLE 22

Improvement of the form of the decollete after application of the 0.04% GGP cream (mean values for 12 volunteers, n = 5 measurements/volunteer)

| | Volume of the hollow of the decollete (mm$^3$) | | Maximal depth of the hollow of the decollete (mm) | | Curve of the decollete; Radius of curvature (mm) | |
|---|---|---|---|---|---|---|
| D10 (en d °) | T0 | T2 m | T0 | T2 m | T0 | T2 m |
| Mean | 1446 +/− 608 | 1359 +/− 569 | 2.27 +/− 1.05 | 2.07 +/− 1.22 | 58.08 +/− 38.07 | 73.54 +/− 49.81 |

TABLE 22-continued

Improvement of the form of the decollete after application of the 0.04% GGP cream (mean values for 12 volunteers, n = 5 measurements/volunteer)

| D10 (en d °) | Volume of the hollow of the decollete (mm³) | | Maximal depth of the hollow of the decollete (mm) | | Curve of the decollete; Radius of curvature (mm) | |
|---|---|---|---|---|---|---|
| | T0 | T2 m | T0 | T2 m | T0 | T2 m |
| 2 m/T0 difference | | −87 | | −0.20 | | −15.46 |
| Change (%) T2 m vs. T0 (→ max) | −6%; p < 0.04 (→ −20%) | | −9%; p < 0.04 (→total smoothing) | | 27%; p < 0.05 (→ 94%) | |

Indeed it is observed with the GGP a decrease of the volume and depth of the hollow of the decollete, and an increase in the radius of curvature of the curve.

Standardized Photographs of the Decollete and Expert Evaluation

Reproducible photographs were taken for the 15 volunteers using the same photographic system as that used for the face. A particular protocol enabled the standardization of the position of the subject's bust for each session.

The T0, T1month and T2months were placed side by side and viewed by an expert panel consisting of 7 judges with the experience in analysis of that type of photograph. To the question: "Compared to T0, the skin appears smoother?" the judges were to reply: Agree/Neither agree nor disagree/Disagree.

The results of the expert evaluation showed a smoothing effect on the bust from T1month (53% of the volunteers) which accentuate at T2months reaching 69% of the volunteers In addition, the volunteers conducted a self-assessment and the results confirmed those obtained by the experts.

4) Study of the Dermal Density Restoration of the Decollete

An ultrasound system DP2200 (Mindray) was used to study the restoration of the cutaneous tissue density at the decollete level. Ultrasound was projected on the area of interest using a 7.5 MHz ultrasound probe. When they encounter a tissue, they are reflected and return a signal, or "echo".

The "sum" of the echoes acquired by the ultrasound probe enable the system the reconstruction of a faithful anatomical image of the zone of interest. From that image, a veritable cross-section of the skin, the tissue thickness can be readily measured.

The objective was to demonstrate an increase of the dermal and epidermal thickness due to restoration of dermal density since collagen I and hyaluronic synthesis is stimulated by the GGP (see the above in vitro results).

TABLE 23

Increase of the thickness of the dermis-epidermis of the decollete after application of the 0.04% GGP cream (mean values for 15 volunteers, n = 6 measurements/volunteer)

| | Dermis-epidermis thickness (mm) | |
|---|---|---|
| | T0 | T 2 months |
| 0.04% GGP cream | 2.53 +/− 0.33 | 2.72 +/− 0.25 |
| Difference (mm) | | 0.19 |
| Change (%); significance; (→Max) | +7.5%; p < 0.01; (→ +22.5%) | |

As shown by the results, the thickness of the dermis-epidermis of the decollete is significantly increased of 0.19 mm at T2 months compared to T0.

The invention claimed is:

1. A method of treating signs of skin aging in a subject in need thereof comprising administering a cosmetic composition comprising geranylgeranyl-2-propanol (GGP) to the skin of the subject, wherein the skin of the subject is normal and healthy, wherein said GGP is between 0.0075% to 0.20% by weight of the total weight of the composition, and wherein said cosmetic composition is applied to the skin of the subject in a daily dosage amount for a time and in a total amount sufficient to cause a cosmetic and non-therapeutic treatment of the skin associated with an enhancement in mechanical properties of dermis and a reinforcement of skin cohesion, or associated with an increase in synthesis of Nidogen 1 in skin of the subject, wherein said increase causes a reparative action on the epidermal/dermal junction in skin.

2. The method of claim 1 wherein said enhancement or said reinforcement is associated with an increase in the synthesis of one or more extracellular matrix proteins in the skin of the subject.

3. The method of claim 2 wherein said one or more extracellular matrix proteins is selected from the group consisting of collagen I, hyaluronic acid, and decorin.

4. The method of claim 1 wherein said enhancement in the mechanical properties is selected from the group consisting of increased skin density, increased skin firmness, increased skin softness and increased skin elasticity.

5. The method of claim 2 wherein said increase in the synthesis of one or more extracellular matrix proteins causes an improvement in visible discontinuities of the skin.

6. The method of claim 5 wherein said improvement is characterized by a decrease in the visibility of wrinkles and fine lines in the skin.

7. A method of delaying signs of skin aging comprising administering a composition comprising geranylgeranyl-2-propanol (GGP) to the skin of a subject in need thereof, wherein the skin of the subject is normal and healthy, wherein said GGP is between 0.0075% to 0.20% by weight of the total weight of the composition, and wherein said composition is applied to the skin for a time and in an amount sufficient to cause a reduction in oxidative stress and free radical damage in the skin.

8. The method of claim 7 wherein said reduction is characterized by a protective effect on telomere length and/or mitochondrial activity.

9. A method of protecting skin from UVB radiation comprising administering a composition comprising geranylgeranyl-2-propanol (GGP) to the skin of a subject in need thereof, wherein the skin of the subject is normal and healthy, wherein said GGP is between 0.0075% to 0.20% by weight of the total weight of the composition, and wherein said composition is applied to the skin for a time and in an amount sufficient to cause a reduction in UV damage to skin keratinocytes.

10. The method of claim 1 wherein said composition is co-administered in combination with one or more compounds selected from the group consisting of mattifying agents, skin lightening agents, skin soothing agents, skin firming agents, anti-redness agents, sunscreens, moisturizing agents, humectants, exfoliating agents, anti-aging agents, anti-wrinkle agents, slimming agents, collagen-stimulating agents, elastin-stimulating agents, volumizing agents, elasticity improving agents, anti-acne agents, anti-inflammatory agents, antioxidants, anti-free radical agents, depigmenting agents, depilatories, peptides, lipopeptides, niacinamide, vitamins, tocopherol, retinol, hexamidine, α-lipoic acid, resveratrol, DHEA, vitamin B3, vitamin E, N-acetyl-Tyr-Arg-O-hexadecylester, Pal-KT, Pal-VGVAPG (SEQ ID NO: 1), Pal-KTTKS (SEQ ID NO: 2), Pal-GHK, Pal-KMO$_2$K, Pal-GQPR (SEQ ID NO: 3).

11. The method of claim 1 wherein the skin to which the composition is administered is selected from the group consisting of skin of the face, lips, neck, neckline, decollete, hands, feet, head, and body.

12. The method of claim 1 wherein said composition is administered using a syringe or micro-canula or by massage into the skin.

13. The method of claim 1 wherein the treatment is administered to the subject in combination with one or more other skin treatment methods.

14. The method of claim 13 wherein said other skin treatment method is selected from the group consisting of luminotherapy, aromatherapy and heat treatments.

15. The method of claim 1 wherein the composition is applied to the skin of the face twice a day for a period of two months.

16. The method of claim 1 wherein the composition is applied to the skin of the decollete twice a day for a period of two months.

17. The method of claim 10 wherein the mattifying agent comprises an extract of *Enantia Chlorantha* bark.

18. The method of claim 10 wherein the skin lightening agent comprises octadecenedioic acid.

19. The method of claim 10 wherein the lipopeptide is lipodipeptide Tyr Arg.

\* \* \* \* \*